United States Patent
Higuchi et al.

(10) Patent No.: US 9,205,415 B2
(45) Date of Patent: Dec. 8, 2015

(54) CATALYST FOR PROPYLENE PRODUCTION, METHOD FOR PRODUCING SAME, AND METHOD FOR PRODUCING PROPYLENE

(75) Inventors: Katsumi Higuchi, Niigata (JP); Saori Kakuta, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 491 days.

(21) Appl. No.: 13/582,516

(22) PCT Filed: Mar. 2, 2011

(86) PCT No.: PCT/JP2011/054802
§ 371 (c)(1),
(2), (4) Date: Nov. 9, 2012

(87) PCT Pub. No.: WO2011/108608
PCT Pub. Date: Sep. 9, 2011

(65) Prior Publication Data
US 2013/0066129 A1 Mar. 14, 2013

(30) Foreign Application Priority Data
Mar. 4, 2010 (JP) ................................. 2010-047917

(51) Int. Cl.
| | | |
|---|---|---|
| B01J 29/06 | (2006.01) | |
| B01J 29/40 | (2006.01) | |
| B01J 29/70 | (2006.01) | |
| B01J 29/80 | (2006.01) | |
| C01B 39/38 | (2006.01) | |
| B01J 35/00 | (2006.01) | |
| C01B 37/02 | (2006.01) | |
| C01B 39/36 | (2006.01) | |
| C07C 1/20 | (2006.01) | |
| C01B 39/40 | (2006.01) | |
| B01J 37/30 | (2006.01) | |

(52) U.S. Cl.
CPC *B01J 29/40* (2013.01); *B01J 29/70* (2013.01); *B01J 29/80* (2013.01); *B01J 35/002* (2013.01); *C01B 37/02* (2013.01); *C01B 39/36* (2013.01); *C01B 39/365* (2013.01); *C01B 39/38* (2013.01); *C01B 39/40* (2013.01); *C07C 1/20* (2013.01); *B01J 37/30* (2013.01); *B01J 2229/186* (2013.01); *B01J 2229/36* (2013.01); *C07C 2529/06* (2013.01); *C07C 2529/40* (2013.01); *C07C 2529/70* (2013.01)

(58) Field of Classification Search
USPC .................... 502/64, 67, 69, 71, 77
See application file for complete search history.

(56) References Cited

U.S. PATENT DOCUMENTS

| | | | |
|---|---|---|---|
| 3,393,007 A | 7/1968 | Fletcher | |
| 3,442,348 A | 5/1969 | Cockerell | |
| 6,187,983 B1 * | 2/2001 | Sun | 585/638 |
| 6,307,117 B1 | 10/2001 | Tsunoda et al. | |
| 7,678,955 B2 * | 3/2010 | Martens et al. | 585/640 |
| 2002/0041845 A1 | 4/2002 | Oku et al. | |
| 2003/0127360 A1 * | 7/2003 | van den Berge et al. | 208/111.01 |
| 2004/0029716 A1 * | 2/2004 | Mohr et al. | 502/67 |
| 2004/0158111 A1 * | 8/2004 | Johnson et al. | 585/467 |
| 2006/0011514 A1 * | 1/2006 | van den Berge et al. | 208/120.01 |
| 2007/0093683 A1 * | 4/2007 | Iaccino et al. | 585/467 |

FOREIGN PATENT DOCUMENTS

| | | | |
|---|---|---|---|
| GB | 2 345 294 | * | 3/2000 |
| JP | 4-217928 | | 8/1992 |
| JP | 2001-58817 | | 3/2001 |
| JP | 2007-302652 | | 11/2007 |
| WO | 00/10948 | | 3/2000 |

OTHER PUBLICATIONS

Machine translation of JP 2007-302652, Nov. 22, 2007.*
"The Conversion of Methanol and Other O-Compounds to Hydrocarbons over Zeolite Catalysts", Journal of Catalysis, vol. 47, 1977, pp. 249-259.
"Selective transformation of methanol into light olefins over a mordenite catalyst: reaction scheme and mechanism", Microporous and Mesoporous Materials, vol. 29, 1999, pp. 79-89.
"Conversion of methanol to hydrocarbons over zeolite H-ZSM-5: On the origin of the olefinic species", Journal of Catalysis, vol. 249, 2007, pp. 195-207.
Search report from International Application No. PCT/JP2011/054802, mail date is Jun. 14, 2011.

* cited by examiner

*Primary Examiner* — Elizabeth Wood
(74) *Attorney, Agent, or Firm* — Greenblum & Bernstein, P.L.C.

(57) ABSTRACT

Disclosed is a propylene production catalyst for producing propylene from one or more selected from a group consisting of methanol, dimethyl ether and olefins having from 4 to 8 carbon atoms. The catalyst comprises a binderless crystalline aluminosilicate shaped body having a silicon/aluminum atomic ratio of from 500 to 10000, in which the crystalline aluminosilicate contains an MFI-type crystal structure and/or an MEL-type crystal structure. The catalyst reduces the production amount of ethylene, paraffin components such as propane, and aromatic components, and increases the propylene yield and the propylene/propane ratio, and the catalyst life is long.

3 Claims, No Drawings

CATALYST FOR PROPYLENE PRODUCTION, METHOD FOR PRODUCING SAME, AND METHOD FOR PRODUCING PROPYLENE

TECHNICAL FIELD

The present invention relates to a catalyst for propylene production which comprises a binderless crystalline aluminosilicate shaped body and which is used for producing propylene from one or more selected from a group consisting of methanol, dimethyl ether and olefins having from 4 to 8 carbon atoms, to a method for producing the catalyst, and to a method for producing propylene by the use of the catalyst.

BACKGROUND ART

Reaction for producing an olefin such as propylene or the like from methanol and/or dimethyl ether by the use of a crystalline aluminosilicate as the catalyst is well known. Non-Patent Reference 1 describes production of olefins from methanol and dimethyl ether in the presence of a crystalline aluminosilicate catalyst having an MFI-type crystal structure. The reaction results described therein include a conversion from methanol and dimethyl ether of from 9.1 to 47.5% and a propylene selectivity of 26.7 to 48.2%; and production of ethylene, butene, paraffins and aromatic components is described therein.

Patent Reference 1 discloses a method for producing an olefin from methanol and/or dimethyl ether by the use of a pentasil-type crystalline aluminosilicate having a silicon/aluminium atomic ratio (hereinafter this is expressed as Si/Al ratio in the specification of the present invention) of at least 10, as the catalyst, wherein the total pressure is from 10 to 90 kPa and the weight ratio of water/methanol is from 0.1 to 1.5. The reference says that the method produces at least 5% by weight of ethylene, at least 35% by weight of propylene and at most 30% by weight of butene, but says that the olefin yield under normal pressure is low and paraffin components and aromatic components such as gasoline and the like are produced as by-products in large quantities. The pentasil type is meant to indicate zeolite having a pentasil structure such as MFI type, MEL type, MOR type, etc.

Specifically, the propylene synthesis reaction from methanol and/or dimethyl ether using a crystalline aluminosilicate as the catalyst produces olefins such as ethylene, butene, paraffins such as methane, ethane, propane, butane, and aromatic components as by-products, except the intended propylene.

According to the description in Non-Patent Reference 2, olefins having 4 or more carbon atoms such as butene of the products except propylene could be converted into propylene by the use of a crystalline aluminosilicate as the catalyst. Accordingly, olefins having 4 or more carbon atoms such as butene can be recycled into the reactor for propylene production from methanol and/or dimethyl ether, and can be converted into propylene. On the other hand, paraffins such as methane, ethane, propane, butane, and ethylene have a lower reactivity than olefins having 4 or more carbon atoms, and therefore, even when recycled into the reactor for propylene production from methanol and/or dimethyl ether, they could not almost be converted into propylene. In addition, propane having a boiling point close to that of propylene, and is therefore defective in that, when the propane production amount increases, then the number of the necessary stages of the distillation column increases and the purification energy cost therefore increase. Further, it is known that the aromatic components are converted into coke that fills the pores of crystalline aluminosilicate to lower the catalytic performance thereof. Non-Patent Reference 3 says that ethylene is produced in the elimination reaction from aromatic compounds.

Accordingly, for propylene production from methanol and/or dimethyl ether, preferred is a catalyst with which the production amount of ethylene, paraffins and aromatic compounds is small, and especially desired is development of a catalyst with which the production amount of ethylene and propane is small.

In general, a crystalline aluminosilicate is hydrothermally produced as a powder thereof having a particle size of around 1 micron or so, starting from an aqueous reaction slurry comprising a silicon compound, an aluminium compound, an alkali metal compound, and a structure directing agent such as tetrapropylammonium hydroxide. Accordingly, for use as a fixed bed catalyst, the compound must be fabricated into a shaped body having a size of around 5 mm, and for use as a fluidized bed catalyst, it must be fabricated into a shaped body of secondary particles having a size of from 50 to 100 microns. In the case, in general, the compound is fabricated with a binder such as clay, alumina or the like.

As a crystalline aluminosilicate shaped body not substantially containing a binder component, there is known a shaped body as produced according to a dry gel conversion process (hereinafter this is referred to as a DGC process in the present specification). Patent Reference 2 discloses a method for producing a crystalline microporous material from a solid component that is precipitated from an alkaline inorganic material mixture liquid containing a crystallization regulating agent (structure directing agent) such as an ammonium ion or an amine, a silicon dioxide ($SiO_2$) component and an aluminium salt.

Patent Reference 3 discloses a binderless MFI-type crystalline aluminosilicate shaped body in which the aluminium content outside the crystal lattice of the binderless crystalline aluminosilicate is at most 3% of all aluminium in the shaped body thereof, and an amination reaction catalyst containing the binderless MFI-type crystalline aluminosilicate shaped body.

CITATION LIST

Patent References

Patent Reference 1: JP-A 4-217928
Patent Reference 2: Japanese Patent 3393007
Patent Reference 3: Japanese Patent 3442348

Non-Patent References

Non-Patent Reference 1: Journal of Catalysis, Vol. 47, pp. 249-259 (1977)
Non-Patent Reference 2: Microporous and Mesoporous Materials, Vol. 29, pp. 79-89 (1999)
Non-Patent Reference 3: Journal of Catalysis, Vol. 249, pp. 195-207 (2007)

SUMMARY OF THE INVENTION

Problems that the Invention is to Solve

The present inventors produced a catalyst by hydrothermally synthetizing a crystalline aluminosilicate powder having an Si/Al ratio of 500 from a starting material of an aqueous reaction slurry that comprises a silicon compound, an aluminium compound, an alkali metal compound and tetrapropylammonium hydroxide, followed by shaping the powder with a binder such as alumina or the like. Using the catalyst, the present inventors tried propylene synthesis reaction from methanol and/or dimethyl ether. However, the propylene yield was low, and by-products of ethylene, paraffin components such as propane, and aromatic components were produced in large quantities. In addition, the crystalline aluminosilicate powder production efficiency was low and the catalyst was not satisfactory as a practicable catalyst.

Consequently, objects of the present invention are to provide a propylene production catalyst with which the production amount of ethylene, paraffin components such as propane, and aromatic components is small in propylene synthesis reaction from methanol and/or dimethyl ether and which is excellent in the propylene yield, the propylene/propane ratio and the catalyst life, and to provide a method for producing the catalyst and a method for producing propylene by the use of the catalyst.

Means for Solving the Problems

The present inventors have assiduously investigated the above-mentioned problems and, as a result, have found that a catalyst comprising a binderless crystalline aluminosilicate shaped body in which the Si/Al ratio falls within a range of from 500 to 10000 can be a propylene production catalyst excellent in the propylene yield, the propylene/propane ratio and the catalyst life, and have completed the present invention.

Specifically, the means for solving the problems with the present invention are the following:

(1) A propylene production catalyst for producing propylene from one or more selected from a group consisting of methanol, dimethyl ether and olefins having from 4 to 8 carbon atoms, which comprises a binderless crystalline aluminosilicate shaped body having a silicon/aluminium atomic ratio of from 500 to 10000 and in which the crystalline aluminosilicate contains an MFI-type crystal structure and/or an MEL-type crystal structure.
(2) The propylene production catalyst of (1), wherein the peak position for the hydroxyl group in the binderless crystalline aluminosilicate shaped body to be detected within a range of from 3715 $cm^{-1}$ to 3735 $cm^{-1}$ in IR spectrometry falls within a range of from 3725 $cm^{-1}$ to 3735 $cm^{-1}$.
(3) The propylene production catalyst of (1) or (2), wherein the crystalline aluminosilicate is an MFI-type crystal structure and/or an MEL-type crystal structure.
(4) The propylene production catalyst of any of (1) to (3), wherein the cation type of the crystalline aluminosilicate is a proton type or an ammonium ion type.
(5) A method for producing propylene from one or more selected from a group consisting of methanol, dimethyl ether and olefins having from 4 to 8 carbon atoms in the presence of the propylene production catalyst of any of (1) to (4).
(6) A method for producing a propylene production catalyst which comprises a binderless crystalline aluminosilicate shaped body having a silicon/aluminium atomic ratio of from 500 to 10000 and in which the crystalline aluminosilicate contains an MFI-type crystal structure and/or an MEL-type crystal structure, the method comprising a conversion step of bringing a starting material shaped body that comprises a solid component containing a silicon component, an aluminium component and a structure directing agent component, into contact with a saturated water vapor-containing atmosphere to thereby convert the silicon component and the aluminium component into a crystalline aluminosilicate.
(7) The method for producing a propylene production catalyst of (6), which includes a firing step of firing the conversion product obtained in the conversion step, in the presence of an alkali metal.
(8) The method for producing a propylene production catalyst of (7), wherein, in the firing step, the conversion product is fired in the presence of an alkali metal in such a manner that the alkali metal/aluminium atomic ratio could fall within a range of from 4 to 200.
(9) The method for producing a propylene production catalyst of (7) or (8), which includes an ion-exchanging step of ion-exchanging the alkali metal in the fired body obtained in the firing step to thereby give a proton-type or ammonium ion-type binderless crystalline aluminosilicate shaped body.

Advantage of the Invention

According to the present invention, there is provided a propylene production catalyst, with which the production amount of ethylene, and paraffin components such as propane is small in propylene synthesis reaction from one or more selected from a group consisting of methanol, dimethyl ether and olefins having from 4 to 8 carbon atoms, and which is excellent in the propylene yield, the propylene/propane ratio and the catalyst life. In addition, since the olefins having from 4 to 8 carbon atoms that are produced as by-products in the propylene synthesis reaction can be recycled in the propylene synthesis reactor and can be converted into propylene, there can be provided a process that realizes a high propylene yield in propylene production from methanol and/or dimethyl ether.

MODE FOR CARRYING OUT THE INVENTION

<Propylene Production Catalyst>

The propylene production catalyst of the present invention comprises a binderless crystalline aluminosilicate shaped body having a silicon/aluminium atomic ratio of from 500 to 10000, in which the crystalline aluminosilicate contains an MFI-type crystal structure and/or an MEL-type crystal structure.

[Crystalline Aluminosilicate]

The crystalline aluminosilicate is a crystalline aluminosilicate molecular sieve or is a compound in which an $SiO_4$ tetrahedron with a silicon atom as the center and four oxygen atoms positioned at the apexes of the center atom, and an $AlO_4$ tetrahedron with an aluminium atom as the center and four oxygen atoms positioned at the apexes of the center atom are three-dimensionally covalently bonded to each other with regularity via the oxygen atoms thereof in such a manner that the atomic ratio of oxygen/(silicon+aluminium) therein could be 2. There are known many crystalline aluminosilicate structures that differ in the pore size and the morphology thereof depending on the bonding mode of the $SiO_4$ tetrahedron and the $AlO_4$ tetrahedron therein. The structure of crystalline aluminosilicate is classified in three-letter codes indicating the individual crystal structures thereof by the International Zeolite Association (IZA). Specifically, the propylene production catalyst of the present invention comprises a binderless crystalline aluminosilicate shaped body containing a crystalline aluminosilicate that contains a structure classified as an MFI-type crystal structure and/or an MEL-type crystal structure in terms of the three-letter code that indicates the crystal structure of crystalline molecular sieve as defined by the International Zeolite Association. The MFI-type crystal structure could be referred to as a ZSM-5-type crystal structure; and the MEL-type crystal structure could be referred to as a ZSM-11-type crystal structure.

The MFI-type crystal structure and the MEL-type crystal structure both have pores having a size of around 5 angstroms and are the same in point of the secondary building unit to constitute the crystal, and therefore, depending on the crystalline aluminosilicate production condition, the two crystal structure types could exist at the same time in one crystal particle (as intergrowth). In the propylene production catalyst of the present invention, the MFI-type crystal structure and/or the MEL-type crystal structure includes a intergrowth morphology of MFI-type crystal structure and MEL-type crystal structure.

In a crystalline aluminosilicate, the electron valence of the $AlO_4$ tetrahedron where an aluminium atom exists in the center is negative, and therefore, the compound could be electrically neutral when bonded to a cation such as proton, ammonium ion, alkali metal ion, alkaline earth metal ion, a rare earth metal ion or the like. The cation exists in the pores of crystalline aluminosilicate, and exhibits a catalytic effect. In the propylene production catalyst of the present invention, the cation type of the binderless crystalline aluminosilicate shaped body is not specifically defined, and for example, the crystalline aluminosilicate therein could be in the form of a proton type, an ammonium ion type, an alkali metal ion type, an alkaline earth metal ion type, a rare earth metal ion type, a transition metal ion type or the like. More preferred is a proton type or an ammonium ion type.

[Binderless Crystalline Aluminosilicate Shaped Body]

So far as containing a structure classified in an MFI-type crystal structure and/or an MEL-type crystal structure, the binderless crystalline aluminosilicate shaped body for the propylene production catalyst of the present invention may contain any other crystal structure of, for example, BEA, MOR, MWW, MTW, FER and the like, as expressed by the three-letter codes each indicating the crystal structure of a crystalline molecular sieve as defined by the International Zeolite Association. However, from the point of the propylene yield in propylene synthesis reaction from methanol and/or dimethyl ether and/or olefins having from 4 to 8 carbon atoms (hereinafter this is expressed as propylene synthesis reaction in the present specification), the propylene production catalyst of the present invention is more preferably a binderless crystalline aluminosilicate shaped body of an MFI-type crystal structure and/or an MEL-type crystal structure (including an intergrowth morphology of MFI-type crystal structure and MEL-type crystal structure, as described above).

The binderless crystalline aluminosilicate shaped body of the propylene production catalyst of the present invention does not substantially contain a binder. Accordingly, the characteristics of the catalyst are that the production amount of ethylene, paraffins such as propane, and aromatic components in the propylene synthesis reaction with the catalyst is small, and the catalyst is excellent in the propylene yield and the propylene/propane ratio.

In the propylene production catalyst of the present invention, the atomic ratio of silicon to aluminium in the binderless crystalline aluminosilicate shaped body falls within a specific range. Concretely, in the propylene production catalyst of the present invention, the atomic ratio of silicon to aluminium in the binderless crystalline aluminosilicate shaped body is, expressed as a silicon/aluminium atomic ratio (Si/Al ratio), from 500 to 10000 (that is, the molar ratio of $SiO_2/Al_2O_3$ is from 1000 to 20000). Preferably, the Si/Al ratio is within a range of from 1000 to 5000 (that is, the molar ratio of $SiO_2/Al_2O_3$ is preferably from 2000 to 10000).

The propylene production catalyst in which the Si/Al ratio in the binderless crystalline aluminosilicate shaped body falls within a range of from 500 to 10000 has characteristics in that the production amount of ethylene, paraffin components such as propane, and aromatic components in the propylene synthesis reaction with the catalyst is small, and the catalyst has a high propylene yield and a high propylene/propane ratio, as compared with the catalyst where the Si/Al ratio is less than 500. The propylene production catalyst in which the Si/Al ratio in the binderless crystalline aluminosilicate shaped body falls within a range of from 1000 to 5000 is more preferred since the production amount of ethylene, paraffin components such as propane, and aromatic components in the propylene synthesis reaction is smaller, and the catalyst has a higher propylene yield and a higher propylene/propane ratio. On the other hand, when the Si/Al ratio is more than 10000, the conversion from methanol and dimethyl ether in the propylene synthesis reaction lowers and the propylene yield therefore lowers.

The measurement method for the Si/Al ratio in the binderless crystalline aluminosilicate shaped body is not specifically defined, for which is employable any ordinary chemical analysis method. For example, a sample solution prepared by dissolving a binderless crystalline aluminosilicate shaped body is analyzed through ICP emission spectrometry (high frequency inductively-coupled plasma emission spectrometry: ICP-AES, ICP-OES), an ICP mass spectrometry (high frequency inductively-coupled plasma mass spectrometry: ICP-MS) or an atomic absorption spectrometry (AAS) thereby measuring the Si/Al ratio therein.

The binderless crystalline aluminosilicate shaped body may contain any other elements of boron, alkaline earth metals, rare earth metals, titanium, zirconium, yttrium, iron, gallium, phosphorus and the like than the main constituent elements of silicon, aluminium and oxygen. These elements may be added in preparing the starting material shaped body or to the binderless crystalline aluminosilicate shaped body, in the form of metal salt solutions, oxides, hydroxides, alkoxides or the like thereof.

Preferably, the peak position for the hydroxyl group in the binderless crystalline aluminosilicate shaped body to be detected in IR spectrometry falls within a specific range. Concretely, the peak position for the hydroxyl group in the binderless crystalline aluminosilicate shaped body to be detected within a range of from $3715\ cm^{-1}$ to $3735\ cm^{-1}$ in IR spectrometry preferably falls within a range of from $3725\ cm^{-1}$ to $3735\ cm^{-1}$.

A crystalline aluminosilicate gives a peak for the hydroxyl group therein to fall within a range of from $3715\ cm^{-1}$ to $3735\ cm^{-1}$ while heated at 200° C. to 500° C. in IR spectrometry. The peak position varies depending on the crystalline aluminosilicate synthesis condition, and may fall within a range of from $3725\ cm^{-1}$ to $3735\ cm^{-1}$ or within a range of from $3715\ cm^{-1}$ to less than $3725\ cm^{-1}$. In the present invention, the propylene production catalyst, in which the peak position for the hydroxyl group in the binderless crystalline aluminosilicate shaped body to be detected within a range of from $3715\ cm^{-1}$ to $3735\ cm^{-1}$ in IR spectrometry falls within a range of from $3725\ cm^{-1}$ to $3735\ cm^{-1}$, is preferred since the propylene yield in propylene synthesis reaction therewith is high and since the catalyst life is long. As opposed to this, the propylene production catalyst, in which the peak position for the hydroxyl group falls within a range of from $3715\ cm^{-1}$ to less than $3725\ cm^{-1}$ (not including $3725\ cm^{-1}$), is not preferred since the propylene yield in propylene synthesis reaction therewith is low and the catalyst life is short.

The hydroxyl group peak falling within a range of from 3715 cm$^{-1}$ to 3735 cm$^{-1}$ in IR spectrometry can be detected by the use of an IR spectrometric apparatus equipped with a device for heating a sample. As the apparatus of the type, for example, preferred is a diffuse reflectance measuring apparatus Spectra-Tech Collector II equipped with a high temperature/vacuum chamber, manufactured by Thermo Nicolay (now Thermo Fisher Scientific). In diffuse reflectance measurement, the sample is analyzed in the form of a powder thereof, and therefore the propylene production catalyst must be fabricated into a powder thereof in analyzing it.

The sample of the binderless crystalline aluminosilicate shaped body to be analyzed in IR spectrometry is a proton-type one prepared by treatment with an aqueous ammonium chloride solution or an aqueous ammonium nitrate solution for ion exchange into an ammonium ion-type one followed by firing to remove ammonia, or a proton-type one prepared by treatment for ion exchange with an aqueous hydrochloric acid solution.

For IR spectrometry, the sample fabricated into a powder is heated. The sample heating temperature is not specifically defined. For example, when heated at 200° C. to 500° C., the sample could readily give a detectable peak for the hydroxyl group therein falling with a range of from 3715 cm$^{-1}$ to 3735 cm$^{-1}$. Even when the sample heating temperature is lower than 200° C., the hydroxyl peak falling within the range could be seen as the case may be; however, in general, crystalline aluminosilicate often absorbs moisture in air when brought into contact with air at a temperature falling within a range of from room temperature to 200° C. and thereby the peak position is often shifted, and therefore, the heating temperature falling within a range of from 200° C. to 500° C. is recommended. The measurement atmosphere in IR spectrometry is not specifically defined. For example, in air or in an inert gas atmosphere such as helium, nitrogen or the like, or in vacuum, the hydroxyl peak falling within a range of from 3715 cm$^{-1}$ to 3735 cm$^{-1}$ can be seen.

<Production Method for Propylene Production Catalyst>

Not specifically defined, the production method for the propylene production catalyst of the present invention preferably includes a step of bringing a starting material shaped body that comprises a solid component containing a silicon component, an aluminium component and a structure directing agent component, or a starting material shaped body that comprises a solid component containing a silicon component, an aluminium component, an alkali metal component and a structure directing agent component, into contact with a saturated water vapor-containing atmosphere to thereby convert nearly the entire amount of the silicon component and the aluminium component into a crystalline aluminosilicate (conversion step). According to the production method, the propylene production catalyst produced does not substantially contain a binder, and as compared with a catalyst which is produced from a crystalline aluminosilicate powder prepared from a conventional aqueous reaction slurry and which therefore requires binder shaping, the catalyst is excellent in that the production amount of ethylene, paraffins such as propane, and aromatic components in propylene synthesis reaction with it is small, and is excellent in the propylene yield and the propylene/propane ratio.

Preferably, the production method for the propylene production catalyst of the present invention includes a step of firing at least once the binderless crystalline aluminosilicate shaped body in the presence of an alkali metal component (firing step). In the firing step, the atomic ratio of alkali metal to aluminium in the binderless crystalline aluminosilicate shaped body is, in terms of alkali metal/aluminium atomic ratio, preferably within a range of from 4 to 200, more preferably within a range of from 10 to 200.

In case where the binderless crystalline aluminosilicate shaped body is fired in the presence of an alkali metal component, the propylene yield in propylene synthesis reaction with the catalyst is high and the catalyst life is long, and therefore the catalyst can be a practicable propylene production catalyst. When the alkali metal/aluminium atomic ratio in the binderless crystalline aluminosilicate shaped body in the firing step is at least 4, the peak position for the hydroxyl group in the binderless crystalline aluminosilicate shaped body to be detected within a range of from 3715 cm$^{-1}$ to 3735 cm$^{-1}$ in IR spectrometry can fall within a range of from 3725 cm$^{-1}$ to 3735 cm$^{-1}$, and therefore the propylene yield in propylene synthesis reaction with the catalyst is higher and the catalyst life is longer, and consequently, the catalyst can be a more practicable propylene production catalyst.

In the firing step, when the alkali metal/aluminium atomic ratio in the binderless crystalline aluminosilicate shaped body is larger, then the propylene yield in propylene synthesis reaction with the catalyst is higher and the catalyst life is longer. Accordingly, the alkali metal/aluminium atomic ratio in the binderless crystalline aluminosilicate shaped body in the firing step is more preferably at least 10.

On the other hand, in the firing step, the upper limit of the alkali metal/aluminium atomic ratio in the binderless crystalline aluminosilicate shaped body is not defined from the above-mentioned two viewpoints, or that is, from the peak position for the hydroxyl group in the binderless crystalline aluminosilicate shaped body to be detected in IR spectrometry, and the propylene yield in propylene synthesis reaction and the catalyst life. However, when the alkali metal/aluminium atomic ratio in the binderless crystalline aluminosilicate shaped body in the firing step is more than 200, it would not provide any problem in the performance of the catalyst for propylene synthesis reaction, but the handleability of the catalyst in the catalyst production process would be poor; and consequently, from the viewpoint of the handleability of the catalyst, the alkali metal/aluminium atomic ratio is preferably at most 200.

Specific Examples of Production Method

The production method for the propylene production catalyst of the present invention is described more concretely hereinunder. Preferably, the production method for the propylene production catalyst of the present invention includes at least three steps of the following first step to third step.

First Step: A step of bringing a starting material shaped body that comprises a solid component containing at least a silicon component, an aluminium component and a structure directing agent component, into contact with a saturated water vapor-containing atmosphere to thereby synthesize a binderless crystalline aluminosilicate shaped body (conversion step).

Second Step: A step of firing the binderless crystalline aluminosilicate shaped body obtained in the first step, preferably in the presence of an alkali metal component (firing step).

Third Step: A step of converting the cation type of the binderless crystalline aluminosilicate shaped body obtained in the second step, into a proton type or an ammonium ion type. (ion-exchange step).

(1) First Step (Conversion Step)

The binderless crystalline aluminosilicate shaped body for the propylene production catalyst of the present invention is synthesized by bringing a starting material shaped body that comprises a solid component containing at least a silicon component, an aluminium component and a structure directing agent component, into contact with a saturated water vapor-containing atmosphere (first step).

The starting material for the silicon component is not specifically defined. As the silicon component, usable here are porous silica support, silica powder, colloidal silica, aqueous sodium silicate solution (silicate soda), alkoxysilane, etc. Above all, a porous silica support is preferred as having a high purity and easy to use. In case where colloidal silica, aqueous sodium silicate solution or alkoxysilane is used as the starting material, the material may be treated with acid or alkali condition to give a silica hydrogel, from which a porous silica support may be prepared for use here as the starting material. During the acid treatment or the alkali treatment, a starting material for the aluminium component may be additionally used to prepare an aluminium component-containing porous silica-alumina support for use herein.

The starting material for the aluminium component is not also specifically defined. As the aluminium component, usable here are aluminium sulfates, aluminium nitrates, aluminium halides, aluminium oxides, aluminium hydroxides, aluminium alkoxides, etc. Also usable are aluminates. Above all, preferred are aluminium sulfate hydrate, aluminium nitrate hydrate, alkali metal aluminates, aluminium hydroxide hydrate, pseudoboehmite and aluminium isopropoxide, as they are easy to use.

The structure directing agent component is not specifically defined, for which preferred is use of tetraalkylammonium salt compounds such as tetramethylammonium hydroxide, methyltriethylammonium hydroxide, tetraethylammonium hydroxide, tetrapropylammonium hydroxide, tetrabutylammonium hydroxide, tetramethylammonium chloride, methyltriethylammonium bromide, tetraethylammonium bromide, tetrapropylammonium bromide, tetrabutylammonium bromide, etc. As combined with these tetraalkylammonium salt compounds, also usable here are organic amines such as normal-propylamine, dinormal-propylamine, trinormal-propylamine, ethylenediamine, diaminopropane, diglycolamine, for producing the binderless crystalline aluminosilicate shaped body containing an MFI-type crystal structure and/or an MEL-type crystal structure. In particular, the tetraalkylammonium salt compound is preferably tetraethylammonium hydroxide, tetrapropylammonium hydroxide, tetrapropylammonium bromide, tetrabutylammonium hydroxide or tetrabutylammonium bromide, since the crystallinity of the crystalline aluminosilicate containing an MFI-type crystal structure and/or an MEL-type crystal structure can be high.

In the production method for the propylene production catalyst of the present invention, the preparation method for the starting material shaped body is not specifically defined. For example, the following methods are employable here.
(Method 1) A method of making an aluminium component, a structure directing agent component and others held by a porous silica support.
(Method 2) A method of making a structure directing agent component and others held by a silica-alumina support.
(Method 3) A method of preparing a starting material shaped body from a silicon component, an aluminium component, a structure directing agent component and others.
(Method 1)

In case where a porous silica support is used as the starting material for the silicon component, the porous silica support is immersed in a solution of other starting materials of an aluminium component, a structure directing agent component, an alkali metal component and others, thereby making those components of the aluminium component, the structure directing agent component, the alkali metal component and others held by the porous silica support to prepare the starting material shaped body. In this case, the individual components may be held by the support all at a time, or may be held sequentially. The order of making the components held by the support is not specifically defined. The alkali metal component may be used or may not be used in the preparation step for the starting material shaped body, as described below.

The shape of the porous silica support is not specifically defined. For example, the support may be used here in the form of a spherical, oval, columnar, ring-like, tabular, sheet-like, honeycomb-like, petal-like one. The size of the porous silica support is not also specifically defined. For example, the size may fall within a range of from 50 μm to 100 mm.

The method of making the aluminium component held by the porous silica support is not specifically defined. For example, a porous silica support is immersed in an aqueous solution or an alcoholic solution of an aluminium component, and thereafter the solvent is removed through decantation, filtration, heating, reduced-pressure heating or the like to thereby make the aluminium component held by the porous silica support. In this, the amount of the aluminium component to be used is preferably such that the Si/Al ratio in the starting material shaped body could fall within a range of from 500 to 10000, since the Si/Al ratio in the crystalline aluminosilicate to be the propylene production catalyst could finally fall within a range of from 500 to 10000. Not specifically defined, the amount of the aqueous solution or the alcoholic solution of the aluminium component to be used for the immersion may be not smaller than the pore volume of the porous silica support in order that the aluminium component could uniformly diffuse in the support, and is preferably from 2 to 5 times the pore volume of the porous silica support. Not also specifically defined, the immersion time for the porous silica support may be such that the aluminium component could diffuse into all the pores of the porous silica support within the immersion time, and in general, the time of from 0.5 hours to 24 hours will be enough.

The method for making the structure directing agent component held by the porous silica support is not specifically defined. For example, a porous silica support is immersed in a structure directing agent, or in an aqueous solution or an alcoholic solution of a structure directing agent, and thereafter the solvent is removed through decantation, filtration, heating, reduced-pressure heating or the like to thereby make the structure directing agent component held by the porous silica support. The amount of the structure directing agent to be held by the porous silica support is not specifically defined. Preferably, the value of the fraction, of which the denominator indicates the molar number of the Si component in the porous silica support and the numerator indicates the molar number of the structure directing agent component held by the porous silica support, falls within a range of from 0.02 to 0.15, more preferably within a range of from 0.04 to 0.08.

The method for making the alkali metal component held by the porous silica support is not specifically defined. For example, a porous silica support is immersed in an aqueous solution or an alcoholic solution of an alkali metal component, and thereafter the solvent is removed through decantation, filtration, heating, reduced-pressure heating or the like to thereby make the alkali metal component held by the porous silica support.
(Method 2)

In case where the starting material shaped body is prepared from a porous silica-alumina support, a porous silica-alumina support is immersed in a solution of a structure directing agent component, an alkali metal component and others to make the structure directing agent component, the alkali metal component and others held by the porous silica-alumina support, thereby preparing the starting material shaped body. The shape and the size of the porous silica-alumina support may be the same as those of the porous silica support. The order of making the structure directing agent component, the alkali metal component and others held by the support, the method of making them held by the support, the components-supporting condition and the timing of the addition step for the alkali metal component may be the same as those in the case where the starting material shaped body is prepared from a porous silica support.

(Method 3)

In the production method for the propylene production catalyst of the present invention, the starting material shaped body may be directly prepared from a silicon component, an aluminium component, a structure directing agent component, an alkali metal component and others. For example, a colloidal silica or a silica powder, and an aluminium compound, a structure directing agent component and an alkali metal component are stirred, mixed, heated and dried to prepare the starting material shaped body. In this case, the obtained starting material shaped body is fabricated into a suitable shape having a suitable size, such as a spherical, columnar, ring-like or the like one, and used in producing a binderless crystalline aluminosilicate shaped body.

In the production method for the propylene production catalyst of the present invention, the starting material shaped body prepared according to the above-mentioned method is brought into contact with a saturated water vapor-containing atmosphere to thereby synthesize a binderless crystalline aluminosilicate shaped body (first step). In this, the temperature of the saturated water vapor is not specifically defined so far as the starting material shaped body can be converted into a binderless crystalline aluminosilicate shaped body with the vapor. Preferred is a temperature falling within a range of from 100° C. to 230° C., at which the crystallization into an MFI-type crystal structure and/or an MEL-type crystal structure could readily occur. More preferred is a temperature falling within a range of from 120° C. to 180° C., at which the crystallinity of the binderless crystalline aluminosilicate shaped body containing an MFI-type crystal structure and/or an MEL-type crystal structure could be higher. The time for which the starting material shaped body is kept in contact with the saturated water vapor-containing atmosphere is not specifically defined. When the starting material shaped body is kept in contact with the vapor for a period of time falling within a range of from 2 hours to 200 hours, then it can be converted into a binderless crystalline aluminosilicate shaped body containing an MFI-type crystal structure and/or an MEL-type crystal structure.

The method and the apparatus for bringing the starting material shaped body into contact with a saturated water vapor-containing atmosphere are not specifically defined but may be any ones in which the starting material shaped body can be converted into a binderless crystalline aluminosilicate shaped body. For example, a starting material shaped body is set in a pressure vessel, water is put into the bottom of the vessel so that it could not be kept in contact with the starting material shaped body, then the vessel is closed and heated in a thermostatic chamber, whereby a binderless crystalline aluminosilicate shaped body can be synthesized therein. In this, the amount of water to be put in the bottom of the vessel is preferably not smaller than the sum total of the saturated water vapor amount, which is determined depending on the crystallization temperature and the pressure vessel capacity, and the amount of the water vapor to be adsorbed by the starting material shaped body. The amount is generally at least 20% by weight relative to the weight of the starting material shaped body. As the case may be, a starting material shaped body may be put into a pressure container, and a saturated water vapor may be fed the pressure container to thereby synthesize a binderless crystalline aluminosilicate shaped body therein.

In the manner as above, nearly the entire amount of the silicon component and the aluminium component used in the starting material are converted into the crystalline aluminosilicate constituting the thus-produced binderless crystalline aluminosilicate shaped body; and while the shape and the size of the starting material shaped body are kept as such, the starting material shaped body is converted into the crystalline aluminosilicate, or that is, the thus-synthesized shaped body does not substantially contain a binder component.

(2) Second Step (Firing Step)

The binderless crystalline aluminosilicate shaped body produced in the first step is fired for two purposes of removing the structure directing agent component and improving thereto the catalytic performance for propylene synthesis reaction. For firing for the former purpose, the alkali metal component is unnecessary; but for firing for the latter purpose, preferably, the binderless crystalline aluminosilicate shaped body is fired in the presence of an alkali metal component in such that the alkali metal/aluminium ratio could fall within a range of from 4 to 200 for further bettering the catalytic performance to be obtained here, as described below. Accordingly, for the purpose of removal of the structure directing agent component and improvement of the propylene synthesis reaction performance, the firing in the presence of an alkali metal component may be attained at a time, or the firing for removal of the structure directing agent component and the firing for improvement of the propylene synthesis reaction improvement in the presence of an alkali metal component may be attained separately.

The atomic ratio of alkali metal to aluminium in the binderless crystalline aluminosilicate shaped body to be fired in the second step is controlled to fall within a range of from 4 to 200 as the atomic ratio of alkali metal/aluminium therein, whereby the propylene production catalyst of the present invention can be a further better catalyst. The timing of the alkali metal component addition step of making an alkali metal component exist in the binderless crystalline aluminosilicate shaped body to be fired in the second step is not specifically defined, so far as the addition could be finished before the final firing in the second step, or that is, the addition may be attained at any time. In addition, the frequency of adding the alkali metal component is not also specifically defined.

For controlling the alkali metal/aluminium atomic ratio in the binderless crystalline aluminosilicate shaped body to be fired in the second step, to fall within a range of from 4 to 200, for example, employable here is a method of adding an alkali metal component in any step of preparing the starting material shaped body that comprises a solid component containing a silicon component, an aluminium component and a structure directing agent, or to the starting material shaped body in such that the alkali metal/aluminium atomic ratio in the binderless crystalline aluminosilicate shaped body to be fired in the second step could fall within a range of from 4 to 200. In this case, the alkali metal component contained in the starting material shaped body is nearly held as such in the binderless crystalline aluminosilicate shaped body that is obtained after contact of the starting material shaped body with a saturated water vapor-containing atmosphere in the first step; however, an alkali metal component may be further added to the binderless crystalline aluminosilicate shaped body obtained in the first step. In particular, in case where the binderless crystalline aluminosilicate shaped body obtained in the first step is washed, a part or all of the alkali metal component in the binderless crystalline aluminosilicate shaped body would dissolve out, and therefore, it is desirable that an alkali metal component is further added to the binderless crystalline aluminosilicate shaped body to be fired in the second step so that the atomic ratio of alkali metal/aluminium in the shaped body could fall within a range of from 4 to 200.

In the first step, even when a starting material shaped body in which the alkali metal/aluminium atomic ratio is less than 4 is kept in contact with a saturated water vapor-containing atmosphere to produce a binderless crystalline aluminosilicate shaped body, it may be good that an alkali metal component is added to the binderless crystalline aluminosilicate shaped body obtained in the first step in order that the alkali metal/aluminium atomic ratio therein could fall within a range of from 4 to 200, prior to the firing in the second step.

It is rather preferred that the amount of the alkali metal component to be contained in the starting shaped body is smaller, since the crystallinity of the MFI-type crystal structure and/or the MEL-type crystal structure of the binderless crystalline aluminosilicate shaped body to be obtained in the first step could be higher; and therefore, it is more desirable that the alkali metal component is not used in the step of preparing the starting material shaped body or in the first step, but is added prior to the firing in the second step. In this case, a more preferred range of the alkali metal amount to be contained in the starting material shaped body or in the binderless crystalline aluminosilicate shaped body in the first step is less than 0.0001 as the atomic ratio of alkali metal/silicon.

(Material of Alkali Metal Component)

In the production method for the propylene production catalyst of the present invention, the alkali metal component to be used is at least one selected from lithium, sodium, potassium, rubidium and cesium. Not specifically defined, the alkali metal compound usable for the component includes, for example, the compounds of lithium, sodium, potassium, rubidium and cesium, such as hydroxides, halides, nitrates, sulfates, acetates, carbonates, bicarbonates, etc. Above all, preferred are the compounds of sodium, potassium and cesium, such as hydroxides, chlorides, nitrates, sulfates, carbonates and bicarbonates as inexpensive and easy to use. One or more of these alkali metal compounds may be used here either singly or as combined. An alkali metal ion may be contained in the structure directing agent such as a solution of tetrapropylammonium hydroxide, and in such a case, the alkali metal ion in the structure directing agent could also be the alkali metal component.

Alkali metal aluminates such as sodium aluminate and potassium aluminate may also be used as the alkali metal component, and these are preferable starting materials as inexpensive, soluble in water and easy to use. An aluminate additionally contain an aluminium component and is therefore used in preparing the starting material shaped body; and in the case, when an alkali metal aluminate alone is used, the alkali metal/aluminium atomic ratio would be less than 4 since the alkali metal/aluminium atomic ratio in the alkali metal aluminate is nearly from 1 to 2, and in the case, special attention should be paid. In such a case, some ways of adding any other alkali metal compound may be tried in order that the alkali metal/aluminium atomic ratio could fall within a range of from 4 to 200.

(Method for Addition of Alkali Metal Component)

The method of adding an alkali metal component is not specifically defined. A method of immersing a starting material shaped body or a binderless crystalline aluminosilicate shaped body in an aqueous or alcoholic solution of an alkali metal compound or in a tetrapropylammonium hydroxide solution containing an alkali metal ion, thereby making the alkali metal held by the shaped body, is preferred as simple. Also employable is a solid-phase ion exchange method of heat-treating a binderless crystalline aluminosilicate shaped body in the presence of an alkali metal compound such as potassium chloride or the like.

(Firing Method)

The firing temperature preferably falls within a range of from 300° C. to 800° C. When the binderless crystalline aluminosilicate shaped body contains a structure directing agent, the firing temperature more preferably falls within a range of from 400° C. to 800° C. as more effective. Not specifically defined, the firing time of from 0.1 hours to 24 hours may be enough. The firing gas atmosphere is not also specifically defined. For example, usable is air atmosphere or an inert gas atmosphere of nitrogen, helium, argon or the like; or an oxygen or air atmosphere diluted with an inert gas such as nitrogen, helium, argon or the like is also usable.

(3) Third Step (Ion-Exchange Step)

The binderless crystalline aluminosilicate shaped body that has been fired in the presence of an alkali metal component contains the alkali metal ion, and therefore before used in propylene synthesis reaction, the shaped body is processed for ion exchange to thereby convert it into a cation-type one such as a proton-type, an ammonium ion-type or the like one (third step).

Not specifically defined, the ion exchange method may be any ordinary one for crystalline molecular sieve. For example, for ammonium ion exchange, the shaped body may be immersed in an aqueous solution of an ammonium salt compound such as ammonium chloride, ammonium nitrate or the like at a temperature falling within a temperature range of from room temperature to 100° C. On the other hand, a solid-phase ion exchange method of firing the binderless crystalline aluminosilicate shaped body in the presence of ammonium chloride or the like is also employable here. From the ammonium ion-type binderless crystalline aluminosilicate shaped body, ammonia is fired away to give a proton-type binderless crystalline aluminosilicate shaped body. The proton-type binderless crystalline aluminosilicate shaped body may also be prepared, for example, through immersion in an aqueous hydrochloric acid solution, an aqueous nitric acid solution or the like at a temperature falling within a temperature range of from room temperature to 100° C.

Examples of Other Production Methods

Further in the production method for the propylene production catalyst of the present invention, even though a binderless crystalline aluminosilicate having an alkali metal/aluminium atomic ratio of less than 4 is fired in the second step, an alkali metal component may be added thereto so that the alkali metal/aluminium atomic ratio in the binderless crystalline aluminosilicate could fall within a range of from 4 to 200 and this may be again fired in the second step. This is because the propylene production catalyst, for which the alkali metal/aluminium atomic ratio in the binderless crystalline aluminosilicate in firing it in the second step is less than 4 and the cation type thereof is converted into a proton-type one or an ammonium ion-type one in the third step, is somewhat poor in the propylene yield in propylene synthesis reaction and in the life performance thereof, however, when an alkali metal component is added thereto in such a manner that the alkali metal/aluminium atomic ratio in the propylene production catalyst could fall within a range of from 4 to 200 and this is again fired in the presence of the alkali metal component, then the propylene yield in propylene synthesis reaction can be increased and the catalyst life can be prolonged.

The step where an alkali metal component is added so that the alkali metal/aluminium atomic ratio in the binderless crystalline aluminosilicate shaped body could fall within a range of from 4 to 200 and this shaped body is fired in the presence of alkali metal component may be carried out after the binderless crystalline aluminosilicate, in which the alkali metal/aluminium atomic ratio is less than 4, has been fired in the second step, or may be carried out after the cation type of the binderless crystalline aluminosilicate shaped body has been converted into a proton-type or ammonium ion-type one in the third step, or may even be carried out after the catalyst has been used in propylene synthesis reaction and has been known to be somewhat poor in the reactivity performance.

The propylene production catalyst of the present invention may also be produced by executing a step of adding an alkali metal component to a binderless crystalline aluminosilicate shaped body, in which the peak position for the hydroxyl group detected within a range of from 3715 $cm^{-1}$ to 3735 $cm^{-1}$ in IR spectrometry falls within a range of from 3715 $cm^{-1}$ to 3725 $cm^{-1}$ (not including 3725 $cm^{-1}$) so that the atomic ratio of alkali metal to aluminium in the binderless crystalline aluminosilicate shaped body could fall within a range of from 4 to 200 as the alkali metal/aluminium atomic ratio therein and effecting firing in the presence of the alkali metal component, and a step of converting the cation type of the resulting binderless crystalline aluminosilicate shaped body into a proton-type or ammonium ion-type one.

The binderless crystalline aluminosilicate shaped body, in which the peak position for the hydroxyl group detected within a range of from 3715 $cm^{-1}$ to 3735 $cm^{-1}$ in IR spectrometry falls within a range of from 3715 $cm^{-1}$ to 3725 $cm^{-1}$ (not including 3725 $cm^{-1}$), is often seen, for example, in a case where the alkali metal/aluminium atomic ratio in the binderless crystalline aluminosilicate in the second step is less than 4 or in a case where the catalytic performance has lowered after long-term propylene synthesis reaction. Even in those cases, when an alkali metal component is added to the binderless crystalline aluminosilicate shaped body so that the alkali metal/aluminium atomic ratio therein could fall within a range of from 4 to 200 and the shaped body is then fired in the presence of the alkali metal component, then the binderless crystalline aluminosilicate shaped body could be converted into a binderless crystalline aluminosilicate shaped body in which the peak position for the hydroxyl group detected within a range of from 3715 $cm^{-1}$ to 3735 $cm^{-1}$ in IR spectrometry falls within a range of from 3725 $cm^{-1}$ to 3735 $cm^{-1}$ and the propylene yield in propylene synthesis production with the catalyst can be increased and the catalyst life can be prolonged.

<Propylene Production Method>

In the present invention, in the presence of the propylene production catalyst obtained according to the above-mentioned method, propylene can be produced from methanol and/or dimethyl ether. In the propylene synthesis reaction using the propylene production catalyst of the present invention, the yield of ethylene, propane and propylene to be produced is nearly on the same level in any case where methanol alone is used as the starting material or dimethyl ether alone is used as the starting material; and therefore, the blend ratio of methanol and dimethyl ether in the starting material for use for propylene production is any arbitrary one, and methanol alone or dimethyl ether alone may be used as the starting material.

In the present invention, propylene may be produced from olefin in the presence of the propylene production catalyst obtained according to the above-mentioned method. For example, using the propylene production catalyst of the present invention, propylene can be produced from an olefin having 4 carbon atoms such as 1-butene or isobutene, or from an olefin starting material having 6 carbon atoms such as 1-hexene (olefin isomerization reaction).

The reaction to produce propylene from methanol and/or dimethyl ether by the use of the propylene production catalyst of the present invention produced olefins such as butene, pentene, hexene and others as by-products. In the present invention, the olefins produced as by-products can be isomerized and converted into propylene in the presence of the propylene production catalyst, and therefore the propylene yield in the entire produce can be thereby increased.

The type of the olefin to be used for isomerization is not specifically defined. The olefins that are produced as by-products in the reaction to produce propylene in the presence of a binderless crystalline aluminosilicate shaped body that contains an MFI-type crystal structure and/or an MEL-type crystal structure are characterized in that the proportion of olefins having from 4 to 8 carbon atoms is large, and therefore from the viewpoint of diffusion of the reaction substances into the pores of the crystal structure, olefins having from 4 to 8 carbon atoms are preferred here.

The origin of the olefin for use for isomerization is not specifically defined, including olefins produced as by-products in propylene synthesis reaction from methanol and/or dimethyl ether, olefins produced as by-products in olefin isomerization, as well as olefins produced in other reaction process such as naphtha cracking, etc. The olefins may be purified and isolated into the individual olefin component in a purification process before using them here, or the olefins for use here may be in the form of a mixture of different types of olefins such as an olefin fraction having from 4 to 8 carbon atoms. The isomerization may be carried out in a reaction apparatus exclusively for isomerization reaction, or may be carried out in a reaction apparatus for producing propylene from methanol and/or dimethyl ether in which the isomerization may be carried out simultaneously with the propylene synthesis reaction from methanol and/or dimethyl ether.

Accordingly, the propylene production method of the present invention includes a method for producing propylene from methanol and/or dimethyl ether in the present of the above-mentioned propylene production catalyst; a method for producing propylene from at least one olefin selected from olefins having from 4 to 8 carbon atoms in the presence of the above-mentioned propylene production catalyst; and a method for producing propylene from a starting material containing one or more selected from a group consisting of methanol, dimethyl ether and olefins having from 4 to 8 carbon atoms in the presence of the above-mentioned propylene production catalyst.

In the propylene production method of the present invention, a starting material containing one or more selected from a group consisting of methanol, dimethyl ether and olefins having from 4 to 8 carbon atoms may be used directly as it is, not diluted, for the propylene synthesis reaction, but is preferably diluted with helium, nitrogen, argon, water vapor or the like prior to the propylene production reaction, as the propylene yield could be higher. Also preferably, ethylene and paraffins having from 2 to 8 carbon atoms, which do not almost trigger propylene synthesis reaction, may be used as the diluent gas, as increasing the propylene yield. In this case, the sum total of the starting material concentration (% by volume) of methanol, dimethyl ether and olefins having from 4 to 8 carbon atoms is preferably within a range of from 25% to 100%. One alone or two or more different types of the diluting gas may be used either singly or as combined.

The reaction apparatus for propylene production in the present invention is not specifically defined, for which employable is any desired reaction apparatus. For example, employable is a fixed bed vapor phase flow-type reaction apparatus or a fluidized bed reaction apparatus. For the fixed bed vapor phase flow-type reaction apparatus, employable are heat-insulation type, multitubular heat-exchange type, intermediate heat-exchange/multistage heat-insulation type, material intermediate feed/multistage heat-insulation type, self-heat-exchange type or the like reactors. The reaction temperature is not specifically defined. From the viewpoint of the propylene yield in propylene synthesis reaction, the temperature preferably falls within a range of from 400° C. to 600° C., more preferably within a range of from 450° C. to 550° C. Also not specifically defined, the reaction pressure is preferably within a range of from 0.01 MPa to 10 MPa as the absolute pressure, more preferably within a range of from 0.05 MPa to 1 MPa. The starting material feeding rate is, in terms of the weight hourly space velocity (WHSV) thereof, preferably within a range of from 0.1 $hr^{-1}$ to 20 $hr^{-1}$, more preferably from 0.5 $hr^{-1}$ to 10 $hr^{-1}$. In this, the weight hourly space velocity (WHSV) means the feeding weight of the starting material per unit weight of the catalyst per hour.

The shape of the catalyst for use for propylene production in the present invention is not specifically defined. For example, a binderless crystalline aluminosilicate shaped body produced in the form of a spherical, oval, columnar, ring-like, tabular, sheet-like, honeycomb-like or petal-like one can be used here directly as it is. If desired, the binderless crystalline aluminosilicate shaped body may be further fabricated into a tablet-like shaped body suitable for the starting material for propylene synthesis reaction. The size of the catalyst is not also specifically defined. A binderless crystalline aluminosilicate shaped body having a suitable size in accordance with the reaction apparatus can be used here, and if desired, the shaped body may be further fabricated.

EXAMPLES

The present invention is described more concretely with reference to the following Examples, however, the present invention is not limited to these Examples.

In Examples and Comparative Examples of the present invention, the physical properties and the reaction performance of the propylene production catalyst were determined as follows.

<Crystal Structure Analysis and Measurement of Degree of Crystallinity>

The crystal structure analysis of the binderless crystalline aluminosilicate shaped body and the measurement of the degree of crystallinity thereof were carried out through powdery X ray diffractiometry (XRD). XRD was as follows: The sample was ground in an agate mortar and dried in a drier set at 110° C. A predetermined amount of the thus-prepared sample was analyzed. For X-ray diffractiometry, used was a powdery X-ray diffractiometry apparatus, M18XCE by Mac Science (now Bruker AXS), in which, using CuKα ray (1.54056 angstroms) as the X ray source, the sample was analyzed within a range of 2θ=2° to 54°. The crystal structure was determined from the peak pattern falling within a range of 2θ=2° to 54°. The degree of crystallinity was determined as follows: The peak intensity appearing within a range of 2θ=23.0° to 23.3° was measured, and based on the peak intensity of UOP's MFI-300 powder ($SiO_2/Al_2O_3$ ratio by mol=300, Si/Al ratio 150), the degree of crystallinity of the sample was expressed as the relative ratio (%) thereof. The peak appearing within a range of 2θ=23.0° to 23.3° for the MFI-type structure corresponds to the (051) plane or the (501) plane of the structure, while the peak appearing within a range of 2θ=23.0° to 23.3° for the MEL-type structure corresponds to the (501) plane of the structure.

<Composition Analysis>

The binderless crystalline aluminosilicate shaped body was quantitatively analyzed for silicon, aluminium and alkali metal contained therein, through ICP emission spectrometry (high frequency inductively-coupled plasma emission spectrometry: ICP-AES, ICP-OES). The sample was ground in an agate mortar and dried in a drier set at 110° C. Just before measurement, the sample was dissolved by microwave decomposition in 60% nitric acid (for microanalysis) and 40% HF (for microanalysis), further diluted with pure water to have a suitable concentration, and analyzed through ICP emission spectrometry. For microwave decomposition, used was a microwave sample pretreatment apparatus ETHOS 1 with a TFM high-pressure decomposition chamber HPV-100 by Milestone General. For the ICP emission spectrometry, used was an ICP emission spectrometry apparatus, VISTA-PRO by Varian Technologies Japan Limited.

<IR Spectrometry>

The binderless crystalline aluminosilicate shaped body was analyzed through IR spectrometry, using an FT-IR spectrometry apparatus, AVATAR 370 and a diffuse reflectance measuring apparatus Spectra-Tech Collector II equipped with a high temperature/vacuum chamber, manufactured by Thermo Nicolay (now Thermo Fisher Scientific). The sample was ground in an agate mortar and dried in a drier set at 110° C. For IR spectrometry, a predetermined amount of the sample was put in the cell of the diffuse reflectance measuring apparatus, and heated in air at 400° C. The IR spectrum was measured for the absorbance (Kubelka-Munk).

<Catalytic Performance Analysis of Propylene Production Catalyst>

The performance test for propylene synthesis reaction was carried out, using a fixed bed vapor phase flow-type reaction apparatus equipped with a starting material tank, a starting material feeding pump, a starting material gas introduction unit, an inert gas introduction unit, a reaction tube (made of quartz glass or made of SUS316, having an inner diameter of 15 mmφ and a length of 300 mm), a cooling unit and a reaction product gas collecting unit. The reaction result was analyzed in a mode of on-line quantitative analysis by introducing the reaction product gas into a gas chromatograph. The methanol conversion and the dimethyl ether conversion in the case where methanol or dimethyl ether was used as the starting material each were calculated according to the following formulae, respectively.

Methanol Conversion(%)=(((weight of starting material methanol)−(weight of methanol in reaction product))/(weight of starting material methanol))×100    (1).

Dimethyl Ether Conversion(%)=(((weight of starting material dimethyl ether)−(weight of dimethyl ether in reaction product))/(weight of starting material dimethyl ether))×100    (2).

The yield of the hydrocarbon compound produced through the reaction was determined by dividing the molar number of carbon in the hydrocarbon produced through the reaction by the molar number of carbon in the starting material, methanol or dimethyl ether, followed by multiplying it by 100. For example, the propylene yield was calculated according to the following formula:

Propylene Yield(c-mol %)=((molar number of propylene produced in reaction×3)/(molar number of starting material methanol×1))×100    (3).

Propylene Yield(c-mol %)=((molar number of propylene produced in reaction×3)/(molar number of starting material dimethyl ether×2))×100    (4).

Typical starting materials and reagents used in synthesis of the propylene production catalysts of Examples and Comparative Examples of the present invention are shown below.
(1) Silica support, CARiACT™, Cat. Code Q-50, nominal particle size 8 to 14 mesh, by Fuji Silysia Chemical-analytical test data: specific surface area 71 m²/g, pore capacity 0.98 ml/g, bulk density 0.42 g/ml, pH 8.0, dry loss 0.5%, mean pore size 47.9 nm.
(2) Tetrapropylammonium hydroxide 40% aqueous solution, by Sachem, product number 746-analytical test data: Assay=40.56 wt. %, K+Na content=3 ppm.
(3) Tetrapropylammonium hydroxide 40% aqueous solution, by Lion Akzo, Cat. Code TPAH-40-analytical test data: Assay=40.0 wt. %, K content=1.0 wt. %.
(4) Aluminium nitrate 9-hydrate, by Kanto Chemical, Cat. No. 01170-00, special grade chemical.
(5) 0.5 mol/L potassium hydroxide solution (N/2), by Kanto Chemical, Cat. No. 32847-08.
(6) Potassium hydroxide, by Kanto Chemical, Cat. No. 32344-00, special grade chemical, purity 86.0%.
(7) Potassium chloride, by Wako Pure Chemicals, Cat. No. 163-03545, special grade chemical.
(8) Sodium aluminate, by Kanto Chemical, Cat. No. 37095-01, Kanto Cica first-class grade chemical, $Al_2O_3$ content=36.5% by mass, $Na_2O$ content=33.0% by mass, $Na_2O/Al_2O_3$ ratio by mol=about 1.5.
<Relationship Between the Amount of Alkali Metal Component Used, and the Physical Properties and the Catalytic Performance, and Addition Step>

Examples 1 to 11 exemplify the relationship between the amount of the alkali metal component used in producing the propylene production catalyst and the physical properties and the catalytic performance. These additionally exemplify the timing of the step of adding the alkali metal component. Table 1 summarizes the type and the amount of the alkali metal compound used in the first step and the second step in Examples (atomic ratio of alkali metal/aluminium), the Si/Al ratio of the propylene production catalyst, the degree of crystallization, the peak position for the hydroxyl group in IR spectrometry, and the result of the propylene synthesis reaction test. The reaction test is as follows: 1.57 g (3.0 ml) of a catalyst of a binderless crystalline aluminosilicate shaped body was charged in the center of the reactor tube, then dimethyl ether (DME) gas was introduced thereinto at a flow rate of 12.7 ml/min and at a weight hourly space velocity (WHSV) of 1.0 hr$^{-1}$, and nitrogen gas was thereinto at a flow rate of 23.7 ml/min. The test condition was at a temperature of 450° C. and under an atmospheric pressure. The dimethyl ether conversion and the propylene yield in the reaction could be higher when the temperature is higher; however, in these Examples, the reaction temperature was kept low in order to compare the catalysts in point of the catalytic performance thereof with ease.

Example 1

Step of Preparing Starting Material Shaped Body 0.0495 g of aluminium nitrate 9-hydrate was dissolved in 33.0 g of pure water, and 20.0 g of a silica support CARiACT™ Q-50 was immersed in the solution for 2 hours. Using a rotary evaporator, water was evaporated away under heat at 70 to 80° C. under reduced pressure, and the resulting material was further dried in a drier at 80° C. for 15 hours to give an aluminium nitrate-supporting silica. Next, the aluminium nitrate-supporting silica was immersed in a solution prepared by diluting 10.02 g of an aqueous solution of 40% tetrapropylammonium hydroxide by Sachem (Cat. No. 746) and 1.06 g of 0.5 mol/L potassium hydroxide solution with 23.0 g of pure water, for 2 hours. Subsequently, using a rotary evaporator, water was evaporated away under reduced pressure under heat at 70 to 80° C., and the resulting material was further dried in a drier at 80° C. for 1 hour thereby to prepare a starting material shaped body that comprises a silica support holding therewith the components of aluminium nitrate, potassium hydroxide and tetrapropylammonium hydroxide. As a result of composition analysis thereof, the compositional ratio of the starting material shaped body was 0.060 TPAOH, 1.0 $SiO_2$, 0.000198 $Al_2O_3$, and 0.0008 $M_2O$, as expressed by the compositional formula of the oxide of each component. The Si/Al ratio was 2525, and the alkali metal/aluminium atomic ratio was 4.0. In this, TPAOH means tetrapropylammonium hydroxide and M means an alkali metal; and the same shall apply hereinunder in this specification.
<Synthesis Step for Binderless Crystalline Aluminosilicate Shaped Body: First Step>

25.2 g of the starting material shaped body was put in a stainless cage, and set in a Teflon™ crucible (inner capacity 100 ml) equipped with a SUS304 jacket and containing 7.0 g of pure water put at the bottom thereof, in such a manner that the starting material shaped body could not be kept in contact with pure water. The jacketed Teflon™ crucible was closed, and heated in a drier at a temperature of 160° C. for 10 hours, whereby the starting material shaped body was kept in contact with a saturated water vapor atmosphere. The heating time was 6 hours. After cooled to room temperature, the resulting white solid was dried at 110° C. for 5 hours. As a result of powdery X-ray diffractiometry thereof, the white solid was known to be formed of a binderless crystalline aluminosilicate shaped body having an MFI-type crystal structure of good crystallinity. In addition, as a result of composition analysis thereof, the alkali metal/aluminium atomic ratio in the binderless crystalline aluminosilicate shaped body was 4.0 and was the same as that in the starting material shaped body.
<Firing Step in the Presence of Alkali Metal Component: Second Step>

The binderless crystalline aluminosilicate shaped body was fired in an air current atmosphere at 550° C. for 4 hours to give 19.8 g of a white solid.
<Cation Exchange Step: Third Step>

The white solid was immersed in an aqueous solution of 2 mol/L ammonium chloride at 70° C. for 2 hours for ammonium ion exchange. The ion exchange operation was repeated three times and the resulting solid was washed until no chloride ion could be detected with aqueous silver nitrate solution. Subsequently, the solid was dried at 110° C. for 5 hours and further fired in an air current atmosphere at 550° C. for 4 hours to give a propylene production catalyst E1 (catalyst E1).
<Physical Properties and Performance Analysis of Catalyst>

The form and the size of the catalyst E1 were the same as the form and the size of the silica support CARiACT™ Q-50 used as the starting material, and as a result of powdery X-ray diffractiometry thereof, the catalyst E1 had a degree of crystallinity of 113%, from which it was known that the catalyst E1 was a binderless crystalline aluminosilicate shaped body having an MFI-type crystal structure of good crystallinity. As a result of composition analysis, the Si/Al ratio was 2525. No alkali metal was detected, and was known to have been removed through ammonium ion exchange. As a result of IR spectrometry, the peak position for the hydroxyl group detected within a range of from 3715 cm$^{-1}$ to 3735 cm$^{-1}$ was 3728.7 cm$^{-1}$. The result of the propylene synthesis reaction on 6 hours after the start of the starting material feeding was: dimethyl ether convention of 100%, and propylene yield of 38.0 c-mol %. The result of the propylene synthesis reaction on 50 hours after the start of the starting material feeding was: dimethyl ether convention of 100.0%, and propylene yield of 36.2 c-mol %. Accordingly, the catalytic performance was good.

Example 2 to Example 4

Propylene production catalysts (catalyst E2, catalyst E3, catalyst E4) were produced in the same manner as in Example 1, except that the amount of the potassium hydroxide to be used in the starting material shaped body preparation step in Example 1 was changed, and the alkali metal/aluminium atomic ratio in the starting material shaped body and the alkali metal/aluminium atomic ratio in the binderless crystalline aluminosilicate shaped body in the firing step in the presence of an alkali metal component in the second step were changed to 10.0, 20.0 and 150.0 respectively. The Si/Al ratio, the degree of crystallinity and the peak position for the hydroxyl group of each catalyst, and the result in propylene synthesis reaction with the catalyst are summarized in Table 1.

Example 5

A propylene production catalyst E5 (catalyst E5) was produced in the same manner as in Example 1, except that 0.0184 g of sodium aluminate was used in place of aluminium nitrate 9-hydrate in Example 1 and the 0.5 mol/L potassium hydroxide solution was not used. In this case, both the alkali metal/aluminium atomic ratio in the starting material shaped body and the alkali metal/aluminium atomic ratio in the binderless crystalline aluminosilicate shaped body in the firing step in the presence of the alkali metal component in the second step were 1.5 as a result of composition analysis. The form and the size of the catalyst E5 were the same as those of the silica support CARiACT™ Q-50 used as the starting material, and as a result of powdery X ray diffractiometry, the degree of crystallinity was 109%. Thus, the catalyst E5 was a binderless crystalline aluminosilicate shaped body having an MFI-type crystal structure of good crystallinity. As a result of composition analysis, the Si/Al ratio was 2525, and no alkali metal was detected. As a result of IR spectrometry, the peak position for the hydroxyl group detected within a range of from 3715 cm$^{-1}$ to 3735 cm$^{-1}$ was 3719.2 cm$^{-1}$. The result of the propylene synthesis reaction on 6 hours after the start of the starting material feeding was: dimethyl ether convention of 100%, and propylene yield of 39.2 c-mol %. The result of the propylene synthesis reaction on 50 hours after the start of the starting material feeding was: dimethyl ether convention of 98.7%, and propylene yield of 33.6 c-mol %. It is known that the catalytic performance on 50 hours was somewhat lowered as compared with that on 6 hours after the start of the starting material feeding.

Example 6

A propylene production catalyst E6 was produced in the same manner as in Example 1, except that 0.5 mol/L potassium hydroxide solution was not used in Example 1. In this case, both the alkali metal/aluminium atomic ratio in the starting material shaped body and the alkali metal/aluminium atomic ratio in the binderless crystalline aluminosilicate shaped body in the firing step in the presence of the alkali metal component in the second step were 0.0058 as a result of composition analysis. The Si/Al ratio, the degree of crystallinity and the peak position for the hydroxyl group of the catalyst E6, and the result in propylene synthesis reaction with the catalyst are summarized in Table 1.

Example 7

A propylene production catalyst E7 was produced in the same manner as in Example 1, except that the amount of potassium hydroxide to be used in the step of preparing the starting material shaped body in Example 1 was changed, and the alkali metal/aluminium atomic ratio in the starting material shaped body and the alkali metal/aluminium atomic ratio in the binderless crystalline aluminosilicate shaped body in the firing step in the presence of the alkali metal component in the second step were changed to 2.0. The Si/Al ratio, the degree of crystallinity and the peak position for the hydroxyl group of the catalyst E7, and the result in propylene synthesis reaction with the catalyst E7 are summarized in Table 1.

Example 8

20.0 g of the catalyst E6 of Example 6 with which the result in propylene synthesis reaction was poor was immersed in an aqueous solution prepared by dissolving 0.10 g of potassium chloride in 33.0 g of pure water, for 2 hours, and subsequently, using a rotary evaporator, water was evaporated away under reduced pressure under heat at 70 to 80° C., and further the resulting material was dried at 110° C. for 5 hours to thereby make potassium chloride held by the catalyst E6. As a result of composition analysis, the alkali metal/aluminium atomic ratio in the potassium chloride-supporting catalyst E6 was 10.2. The potassium chloride-supporting catalyst E6 was fired in an air current atmosphere at 550° C. for 4 hours, and then subjected to cation exchange in the same manner as in the third step in Example 1 thereby producing a propylene production catalyst E8 (white solid). The form and the size of the catalyst E8 were the same as those of the silica support CARiACT™ Q-50 used as the starting material, and as a result of powdery X ray diffractiometry, the degree of crystallinity was 118. Thus, the catalyst E8 was a binderless crystalline aluminosilicate shaped body having an MFI-type crystal structure of good crystallinity. As a result of composition analysis, the Si/Al ratio was 2525, and no alkali metal was detected. As a result of IR spectrometry, the peak position for the hydroxyl group detected within a range of from 3715 cm$^{-1}$ to 3735 cm$^{-1}$ was 3729.5 cm$^{-1}$. The result of the propylene synthesis reaction on 6 hours after the start of the starting material feeding was: dimethyl ether convention of 100%, and propylene yield of 38.4 c-mol %. The result of the propylene synthesis reaction on 50 hours after the start of the starting material feeding was: dimethyl ether convention of 100%, and propylene yield of 38.8 c-mol %. Thus, the catalytic performance was good.

Example 9

A starting material shaped body comprising a silica support that supports aluminium nitrate and tetrapropylammonium hydroxide was prepared in the same manner as that for the preparation of the starting material shaped body in Example 6, in which the 0.5 mol/L potassium hydroxide solution used in the step of preparing the starting material shaped body in Example 1 was not used. As a result of composition analysis, the composition ratio of the starting material shaped body was 0.060 TPAOH, 1.00 $SiO_2$, 0.0001980 $Al_2O_3$, and 0.00000120 $M_2O$, as expressed by the compositional formula of the oxide of each component. The Si/Al ratio was 2525, and the alkali metal/aluminium atomic ratio was 0.0058. In the same manner as that for the first step in Example 1, the synthesis step for a binderless crystalline aluminosilicate shaped body was carried out to produce a pale brownish white solid. As a result of powdery X ray diffractiometry, the pale brownish white solid had an MFI-type crystal structure of good crystallinity, and the production of a binderless crystalline aluminosilicate shaped body was known. 22.8 g of the pale brownish white solid was immersed in an aqueous solution prepared by dissolving 0.20 g of potassium chloride in 33.0 g of pure water, for 2 hours, and subsequently, using a rotary evaporator, water was evaporated away under reduced pressure under heat at 70 to 80° C., and further the resulting material was dried at 110° C. for 5 hours thereby producing a potassium chloride-supporting binderless crystalline aluminosilicate shaped body. As a result of composition analysis, the alkali metal/aluminium atomic ratio in the binderless crystalline aluminosilicate shaped body at this point was 20.3. The shaped body contained a tetrapropylammonium ion as the structure directing agent component. The potassium chloride-supporting shaped body was fired in an air current atmosphere at 550° C. for 4 hours to give 19.7 g of a white solid, and then subjected to cation exchange in the same manner as in the third step in Example 1 thereby producing a propylene production catalyst E9 (white solid). The Si/Al ratio, the degree of crystallinity and the peak position for the hydroxyl group of the catalyst E9, and the result in propylene synthesis reaction with the catalyst are summarized in Table 1.

Example 10

In the same manner as in Example 9, the starting material shaped body was prepared and processed in the first step to give a binderless crystalline aluminosilicate shaped body. Next, different from the way in Example 9, the shaped body was, without being processed for supporting potassium chloride therewith, fired in an air current atmosphere at 550° C. for 4 hours to remove the tetrapropylammonium ion of the structure directing agent component. As a result of composition analysis, the alkali metal/aluminium atomic ratio in the binderless crystalline aluminosilicate shaped body at this point was 0.0058 like in the starting material shaped body. The binderless crystalline aluminosilicate shaped body was processed so as to support potassium chloride therewith in such a manner that the alkali metal/aluminium atomic ratio therein could be 50.0. The potassium chloride-supporting shaped body was fired in an air current atmosphere at 400° C. for 4 hours, and then subjected to cation exchange in the same manner as in the third step in Example 1 thereby producing a propylene production catalyst E10. The Si/Al ratio, the degree of crystallinity and the peak position for the hydroxyl group of the catalyst E10, and the result in propylene synthesis reaction with the catalyst are summarized in Table 1.

Example 11

A propylene production catalyst E11 was produced in the same manner as in Example 9, except that the potassium chloride supporting amount in Example 9 was changed so that the alkali metal/aluminium atomic ratio in the binderless crystalline aluminosilicate shaped body could be 2.0. The Si/Al ratio, the degree of crystallinity and the peak position for the hydroxyl group of the catalyst E11, and the result in propylene synthesis reaction with the catalyst are summarized in Table 1.

From the results in Examples 1 to 11 shown in Table 1, it is known that when a binderless crystalline aluminosilicate shaped body having a specific alkali metal component amount, or that is, having an alkali metal/aluminium atomic ratio to fall within a range of from 4 to 200 is fired, then a propylene production catalyst more excellent in the propylene yield in propylene synthesis reaction and in the catalyst life can be obtained. In addition, it is known that the alkali metal component amount corresponds to the peak position in IR spectrometry. It is known that the alkali metal component may be used in the step of preparing the starting material shaped body, or may be added to the binderless crystalline aluminosilicate shaped body produced after contact of the starting material shaped body with saturated water vapor, or may also be added to the binderless crystalline aluminosilicate shaped body from which the structure directing agent component has been removed. It is also known that even the catalyst of which the reactivity performance is somewhat poor can be enhanced to have an excellent reactivity performance by firing it in the presence of an alkali metal component falling within the above-mentioned range.

<Type of Alkali Metal Compound, and Catalyst Production Method>

Examples 12 to 17 are to exemplify and demonstrate the type of alkali metal compound, the method for preparing starting material shaped body, and the heat treatment condition in the first step. Table 2 summarizes the type and the amount of the alkali metal compound used in the first step and the second step in Examples (alkali metal/aluminium atomic ratio), the Si/Al ratio, the degree of crystallinity and the peak position for the hydroxyl group in IR spectrometry of the propylene production catalyst and the results of the propylene synthesis reaction test with the catalyst. The reaction test was carried out in the same manner as in Examples shown in Table 1.

Example 12

A propylene production catalyst E12 was produced in the same manner as in Example 1, except that 0.112 g of lithium chloride (Wako Pure Chemicals' Cat. No. 127-01165, special grade chemical) was used in place of the 0.5 mol/L potassium hydroxide solution in Example 1, and the heat treatment condition in the first step was changed to 180° C. and 10 hours. The alkali metal/aluminium atomic ratio in the first and second steps, the Si/Al ratio, the degree of crystallinity and the peak position for the hydroxyl group of the catalyst E12, and the result in propylene synthesis reaction with the catalyst are summarized in Table 2.

Example 13

A propylene production catalyst E13 was produced in the same manner as in Example 1, except that 0.267 g of potassium nitrate (Wako Pure Chemicals' Cat. No. 160-04035, special grade chemical) was used in place of the 0.5 mol/L potassium hydroxide solution in Example 1, and the heat treatment condition in the first step was changed to 120° C. and 30 hours. The alkali metal/aluminium atomic ratio in the first and second steps, the Si/Al ratio, the degree of crystallinity and the peak position for the hydroxyl group of the catalyst E13, and the result in propylene synthesis reaction with the catalyst are summarized in Table 2.

Example 14

20.0 g of a silica powder by Nippon Aerosil (Aerosil™ 200 powder), 10.02 g of an aqueous solution of 40% tetrapropylammonium hydroxide by Sachem (Cat. No. 746), an aqueous solution of 0.0415 g of aluminium sulfate 14 to 18-hydrate (by Kanto Chemical, Cat. No. 01186-00, Kanto Cica special grade chemical), and 5.28 g of a solution of 0.5 mol/L sodium hydroxide (N/2) (by Kanto Chemical, Cat. No. 37848-08) were stirred and mixed to prepare a white precipitate slurry. The slurry was dried in a drier at 80° C. to give a white solid. The solid was compression-molded to give a starting material shaped body, which was then processed according to the same operation as in the first step, the second step and the third step in Example 1 to give a propylene production catalyst E14. The alkali metal/aluminium atomic ratio in the first and second steps, the Si/Al ratio, the degree of crystallinity and the peak position for the hydroxyl group of the catalyst E14, and the result in propylene synthesis reaction with the catalyst are summarized in Table 2.

Example 15

While 90 g of an aqueous solution of 4 mol/L sodium hydroxide (by Wako Pure Chemicals, Cat. No. 198-13765, special grade chemical) was dropwise added to a solution of 60 g of 20% colloidal silica (Snowtex N) by Nissan Chemical, this was stirred and mixed to prepare a white precipitate gel. Subsequently, an aqueous solution of 20% sulfuric acid was added thereto until the pH of the precipitate gel dispersion could reach around 6. The precipitate was separated through filtration, washed with water and dried overnight in a drier at 110° C. The obtained silica powder was immersed in an aqueous solution of aluminium nitrate, and then dried overnight in a drier at 110° C. The powder was compression-molded, then fired at 300° C. for 3 hours to give 20.0 g of a silica-alumina support. 10.02 g of an aqueous solution of 40% tetrapropylammonium hydroxide by Sachem (Cat. No. 746) was applied thereto to make it support the tetrapropylammonium component therewith to be a starting material shaped body. This was processed in the same manner as in the first step in Example 1 to give a binderless crystalline aluminosilicate shaped body, then an aqueous solution of cesium carbonate ($Cs_2CO_3$, by Wako Pure Chemicals, Cat. No. 038-06545, Wako first-class grade chemical) was applied thereto to make it support cesium carbonate therewith. This was processed in the same manner as in the second step and the third step in Example 1 to give a propylene production catalyst E15. The alkali metal/aluminium atomic ratio in the first and second steps, the Si/Al ratio, the degree of crystallinity and the peak position for the hydroxyl group of the catalyst E15, and the result in propylene synthesis reaction with the catalyst are summarized in Table 2.

Example 16

A propylene production catalyst E16 was produced in the same manner as in Example 1 except that the same amount of an aqueous solution of 40% tetrapropylammonium hydroxide by Lion Akzo (Cat. Code TPAH-40) was used in place of the aqueous solution of 40% tetrapropylammonium hydroxide by Sachem (Cat. No. 746) in Example 1 and the 0.5 mol/L potassium hydroxide solution was not used. In this case, TPAH-40 contained a potassium component, and therefore, the alkali metal/aluminium atomic ratio in the solid before the firing in the second step was 21.4. The alkali metal/aluminium atomic ratio in the first and second steps, the Si/Al ratio, the degree of crystallinity and the peak position for the hydroxyl group of the catalyst E16, and the result in propylene synthesis reaction with the catalyst are summarized in Table 2.

Example 17

A propylene production catalyst E17 was produced in the same manner as in Example 5 except that the binderless crystalline aluminosilicate shaped body in Example 5 was processed so as to support before the firing in the second step, potassium chloride therewith in an amount to have an alkali metal/aluminium atomic ratio of 20.0. As a result of composition analysis, the alkali metal/aluminium atomic ratio in the starting material shaped body was 1.5, and the alkali metal/aluminium atomic ratio in the binderless crystalline aluminosilicate shaped body in the firing step in the presence of the alkali metal component in the second step was 20.0. The Si/Al ratio, the degree of crystallinity and the peak position for the hydroxyl group of the catalyst E17, and the result in propylene synthesis reaction with the catalyst are summarized in Table 2.

From the results in Examples 12 to 17 shown in Table 2, it is known that an alkali metal compound with lithium, sodium, potassium or cesium can be used in production of the propylene production catalyst of the present invention. It is also known that sodium aluminate may be combined with any other alkali metal component for producing herein a catalyst having a better propylene production ability.

<Firing Temperature in the Presence of Alkali Metal Component>

Examples 10 and 18 to 20 are to demonstrate the influence of the firing temperature in the presence of an alkali metal component. The reaction test was carried out in the same manner as in Example 1.

Example 18

A propylene production catalyst E18 was produced in the same manner as in Example 10 except that a binderless crystalline aluminosilicate shaped body that supports potassium chloride was fired in an air current atmosphere at 300° C. for 4 hours in Example 10. As a result of composition analysis, the Si/Al ratio was 2525. The peak position for the hydroxyl group in IR spectrometry was 3727.8 $cm^{-1}$. The result of the propylene synthesis reaction on 50 hours after the start of the starting material feeding was: dimethyl ether convention of 100.0%, and propylene yield of 38.4 c-mol %. Accordingly, the catalytic performance was good.

Example 19

A propylene production catalyst E19 was produced in the same manner as in Example 10 except that a binderless crystalline aluminosilicate shaped body that supports potassium chloride was fired in an air current atmosphere at 650° C. for 4 hours in Example 10. As a result of composition analysis, the Si/Al ratio was 2525. The peak position for the hydroxyl group in IR spectrometry was 3729.0 $cm^{-1}$. The result of the propylene synthesis reaction on 50 hours after the start of the starting material feeding was: dimethyl ether convention of 100.0%, and propylene yield of 38.9 c-mol %. Accordingly, the catalytic performance was good.

Example 20

A propylene production catalyst E20 was produced in the same manner as in Example 10 except that a binderless crystalline aluminosilicate shaped body that supports potassium chloride was fired in an air current atmosphere at 200° C. for 4 hours in Example 10. As a result of composition analysis, the Si/Al ratio was 2525. The peak position for the hydroxyl group in IR spectrometry was 3719.2 $cm^{-1}$. The result of the propylene synthesis reaction on 50 hours after the start of the starting material feeding was: dimethyl ether convention of 96.8%, and propylene yield of 29.7 c-mol %. The catalytic performance was somewhat poor.

<Relationship Between Si/Al Ratio in Propylene Production Catalyst and Catalytic Performance>

Examples 16, 21 to 24, and Comparative Examples 1 and 2 are to demonstrate examples of propylene synthesis reaction from dimethyl ether using a propylene production catalyst produced by changing the Si/Al ratio therein. Example 25 is to demonstrate an example of reaction with a catalyst having an MEL-type crystal structure. Comparative Example 3 is to demonstrate an example of propylene synthesis reaction using a crystalline aluminosilicate produced according to a conventional method of using an aqueous reaction slurry. Table 3 summarizes the Si/Al ratio, the crystal structure, the degree of crystallinity and the peak position for the hydroxyl group in IR spectrometry of the catalysts of Examples and Comparative Examples, and the results in propylene synthesis reaction with each of those catalysts. The reaction test was carried out in the same manner as in Examples shown in Table 1.

Example 21 to Example 24

Propylene production catalysts (catalyst E21, catalyst E22, catalyst E23 and catalyst E24) were produced in the same manner as in Example 16, except that the amount of aluminium nitrate 9-hydrate in Example 16 was changed, and the Si/Al ratio fed for the starting shaped body was changed to 500, 1000, 1500 or 5000. As a result of composition analysis, the Si/Al ratio in the propylene production catalysts was 500, 1000, 1500 or 5000, respectively, which was the same as the Si/Al ratio for the starting shaped body. The Si/Al ratio, the crystal structure, the degree of crystallinity and the peak position for the hydroxyl group of each catalyst, the result in propylene synthesis reaction with the catalyst, the propylene/ethylene ratio (c-mol ratio) and the propylene/propane ratio (c-mol ratio) are summarized in Table 3.

Comparative Example 1

A propylene production catalyst C1 was produced in the same manner as in Example 16, except that the amount of aluminium nitrate 9-hydrate to be used in Example 16 was changed, the Si/Al ratio to be fed for the starting shaped body was 250, and the shaped body was processed to support potassium chloride therewith prior to firing thereof in the presence of an alkali metal in the second step to thereby change the alkali metal/aluminium atomic ratio to 10.0. The Si/Al ratio, the crystal structure, the degree of crystallinity and the peak position for the hydroxyl group of the catalyst C1, the result in propylene synthesis reaction with the catalyst, the propylene/ethylene ratio (c-mol ratio) and the propylene/propane ratio (c-mol ratio) are summarized in Table 3.

Comparative Example 2

A propylene production catalyst C2 was produced in the same manner as in Example 16, except that aluminium nitrate 9-hydrate was not used in Example 16. As a result of composition analysis, the Si/Al ratio in the catalyst C2 was 15000. The Si/Al ratio, the crystal structure, the degree of crystallinity and the peak position for the hydroxyl group of the catalyst C2, the result in propylene synthesis reaction with the catalyst, the propylene/ethylene ratio (c-mol ratio) and the propylene/propane ratio (c-mol ratio) are summarized in Table 3.

Example 25

A propylene production catalyst E25 was produced in the same manner as in Example 3, except that 13.0 g of an aqueous solution of 40% tetrabutylammonium hydroxide by Sachem was used in place of the aqueous solution of 40% tetrapropylammonium hydroxide by Sachem (Cat. No. 746) in Example 3. The Si/Al ratio, the crystal structure, the degree of crystallinity and the peak position for the hydroxyl group of the catalyst E25, the result in propylene synthesis reaction with the catalyst, the propylene/ethylene ratio (c-mol ratio) and the propylene/propane ratio (c-mol ratio) are summarized in Table 3.

Comparative Example 3

With reference to a patent reference, JP-A 2001-72411, an MFI-type crystalline aluminosilicate powder was produced according to the process mentioned below. 39.9 g of an aqueous solution of 40% tetrapropylammonium hydroxide by Sachem (Cat. No. 746), 72.8 g of tetraethoxysilane and 193.4 g of pure water were mixed, and drastically stirred for 2 hours. 10 ml of an aqueous solution of 0.26 g of aluminium nitrate 9-hydrate was added to the solution to give an aqueous slurry, and using an autoclave (inner capacity 0.5 L) equipped with a stirrer, this was heated at a temperature of 105° C. for 96 hours under the self-pressure. The resulting white slurry was centrifuged to give a white precipitate. Water was added to the precipitate, and the centrifugation and washing was repeated until the pH of the supernatant could reach 7. After dried overnight at 80° C., this was fired in an air current atmosphere at 600° C. for 4 hours to give 15.1 g of a white powder. The yield of the white powder was 72% by weight of the theoretical yield as calculated from the amount of silicon and aluminium contained in the starting materials of ethoxyethoxysilane and aluminium 9-hydrate. This was ammonium ion-exchanged and fired in the same manner as in the cation exchange step in Example 1 to give a catalyst C3. As a result of powdery X ray diffractiometry thereof, the degree of crystallinity of the catalyst was 111%, and it was known that the catalyst C3 is an MFI-type crystalline aluminosilicate of good crystallinity. As a result of composition analysis, the Si/Al ratio was 500. In the propylene synthesis reaction test, used was one produced by shaping the catalyst C3 along with JGC Catalysts and Chemicals' alumina sol, Cataloid-AP in an amount of 20% by weight of the catalyst C3, followed by firing and granulating the shaped body. The Si/Al ratio, the crystal structure, the degree of crystallinity and the peak position for the hydroxyl group of the catalyst C3, the result in propylene synthesis reaction with the catalyst, and the propylene/ethylene ratio (c-mol ratio) and the propylene/propane ratio (c-mol ratio) are summarized in Table 3.

From the results in Examples 16, 21 to 24 and Comparative Examples 1 and 2, it is known that the propylene production catalysts of a binderless crystalline aluminosilicate shaped body in which the Si/Al ratio falls within a range of from 500 to 10000 and which has an MFI-type or MEL-type crystal structure are superior to other catalysts in which the Si/Al ratio is less than 500 in that the production amount of ethylene and paraffins such as propane is small, the propylene yield is high and the propylene/propane ratio (c-mol ratio) is high. Comparative Example 3 is an example of producing an MFI-type crystalline aluminosilicate having an Si/Al ratio of 500; however, in this, the result of propylene synthesis reaction was poor owing to the alumina binder component used for shaping.

Example of Catalyst Life Test

Example 26

This is a reaction test with the catalyst E16 of Example 16 at a temperature of 500° C. under atmospheric pressure, in which a vapor of dimethyl ether was fed to a reactor at a weight hourly space velocity (WHSV) of 2.0 $hr^{-1}$. The reaction gas composition was dimethyl ether/nitrogen ratio by volume of 60/40. Table 4 shows the yield of each component, the propylene/ethylene ratio (c-mol ratio) and the propylene/propane ratio (c-mol ratio) on 100 hours, 500 hours and 1000 hours. After reaction for 1000 hours with the catalyst E16, the dimethyl ether conversion was not less than 99% and the propylene yield was 42%, and the catalyst was good.

Reaction Example by use of Methanol

Example 27

This is a reaction test with the catalyst E16 of Example 16 at a temperature of 500° C. under atmospheric pressure, in which methanol was fed to a reactor at a weight hourly space velocity (WHSV) of 2.4 $hr^{-1}$. The reaction gas composition was methanol/nitrogen ratio by volume of 75/25. On 500 hours in reaction, the methanol conversion was 100.0%, the propylene yield was 46.8%, the propylene/ethylene ratio (c-mol ratio) was 13.4, and the propylene/propane ratio (c-mol ratio) was 707. The results are comparable to or higher than those in the reaction starting from dimethyl ether.

Example of Propylene Production from Ethylene, Butene and Hexene

Example 28

This is a reaction test with the catalyst E16 of Example 16 at a temperature of 500° C. under atmospheric pressure, in which 1-butene was fed to a reactor at a weight hourly space velocity (WHSV) of 1.0 $hr^{-1}$. The reaction gas composition was 1-butene/nitrogen ratio by volume of 50/50. Table 5 summarizes the reaction tube outlet port gas composition on 24 hours in reaction.

Example 29

This is the same as Example 28 except that 1-hexene was used in place of 1-butene in Example 28.

Example 30

This is the same as Example 28 except that ethylene was used in place of 1-butene in Example 28. It is known that ethylene reacted little with the propylene production catalyst of the present invention.

Reaction Example by Use of Mixed Material of Methanol, Dimethyl Ether, Butene and Ethylene Example 31

This is a reaction test with the catalyst E16 of Example 16 at a temperature of 550° C. under atmospheric pressure, in which a mixed starting material having a reaction gas composition (% by volume) of dimethyl ether/ethylene/isobutene/water=46/3/6/45 was fed to a reactor. WHSV of dimethyl ether was 1.0 $hr^{-1}$ and WHSV of isobutene was 0.16 $hr^{-1}$. Table 6 summarizes the reaction tube outlet port gas composition on 24 hours in reaction. The dimethyl ether conversion was 100.0% and the propylene yield was 47.5%; and the data are the same as those in Example 26 in which dimethyl ether alone was used as the starting material.

Example 32

This is a reaction test with the catalyst E16 of Example 16 at a temperature of 550° C. under atmospheric pressure, in which a mixed starting material having a reaction gas composition (% by volume) of methanol/ethylene/1-butene=91/3/6 was fed to a reactor. WHSV of methanol was 2.0 $hr^{-1}$ and WHSV of isobutene was 0.23 $hr^{-1}$. Table 6 summarizes the reaction tube outlet port gas composition on 24 hours in reaction. The methanol conversion was 100.0% and the propylene yield was 47.2%; and the data are the same as those in Example 27 in which methanol alone was used as the starting material.

TABLE 1

| | First Step(*1) | | Second Step(*2) | | | | Hydroxyl Group | | Reaction Result on 6 hours(*5) | | Reaction Result on 50 hours(*5) | |
| --- | --- | --- | --- | --- | --- | --- | --- | --- | --- | --- | --- | --- |
| Example | Alkali Metal Compound | Alkali Metal/Al Ratio | Alkali Metal Compound | Alkali Metal/Al Ratio | Si/Al Ratio | Degree of Crystallinity (%) | Peak Position ($cm^{-1}$) | | DME Conversion (%) | Propylene Yield (c-mol %) | DME Conversion (%) | Propylene Yield (c-mol %) |
| Example 1 | KOH | 4.0 | none | 0 | 2525 | 113 | 3728.7 | | 100.0 | 38.0 | 100.0 | 36.2 |
| Example 2 | KOH | 10.0 | none | 0 | 2525 | 101 | 3729.8 | | 100.0 | 38.9 | 100.0 | 39.2 |

TABLE 1-continued

| Example | First Step(*1) Alkali Metal Compound | Alkali Metal/Al Ratio | Second Step(*2) Alkali Metal Compound | Alkali Metal/Al Ratio | Si/Al Ratio | Degree of Crystallinity (%) | Hydroxyl Group Peak Position (cm$^{-1}$) | Reaction Result on 6 hours(*5) DME Conversion (%) | Propylene Yield (c-mol %) | Reaction Result on 50 hours(*5) DME Conversion (%) | Propylene Yield (c-mol %) |
|---|---|---|---|---|---|---|---|---|---|---|---|
| Example 3 | KOH | 20.0 | none | 0 | 2525 | 104 | 3728.7 | 100.0 | 38.7 | 100.0 | 39.5 |
| Example 4 | KOH | 150.0 | none | 0 | 2525 | 105 | 3729.0 | 100.0 | 38.5 | 100.0 | 38.7 |
| Example 5 | sodium aluminate | 1.5 | none | 0 | 2525 | 109 | 3719.2 | 100.0 | 39.2 | 98.7 | 33.6 |
| Example 6 | none | 0.0058 | none | 0 | 2525 | 118 | 3719.9 | 100.0 | 38.8 | 95.1 | 28.0 |
| Example 7 | KOH | 2.0 | none | 0 | 2525 | 116 | 3719.2 | 100.0 | 39.8 | 99.2 | 32.4 |
| Example 8 | none | 0.0058 | KCl | 10.2(*3) | 2525 | 118 | 3729.5 | 100.0 | 38.4 | 100.0 | 38.8 |
| Example 9 | none | 0.0058 | KCl | 20.3 | 2525 | 119 | 3729.2 | 100.0 | 38.5 | 100.0 | 39.1 |
| Example 10 | none | 0.0058 | KCl | 50.0(*4) | 2525 | 117 | 3728.8 | 100.0 | 38.6 | 100.0 | 38.9 |
| Example 11 | none | 0.0058 | KCl | 2.0 | 2525 | 116 | 3719.1 | 100.0 | 39.0 | 98.7 | 31.4 |

(*1)Alkali metal compound used in the step of preparing the starting material shaped body, and alkali meta/aluminium atomic ratio.
(*2)Alkali metal compound added to binderless crystalline aluminosilicate shaped body, and alkali meta/aluminium atomic ratio.
(*3)Potassium chloride was added to the catalyst E6 (proton-type binderless crystalline aluminosilicate) in Example 6.
(*4)Potassium chloride was added to the binderless crystalline aluminosilicate after removal of structure directing agent by firing.
(*5)Reaction temperature: 450° C., WHSV of DME: 1.0 hr$^{-1}$.

TABLE 2

| Example | First Step(*1) Alkali Metal Compound | Alkali Metal/Al Ratio | Second Step(*2) Alkali Metal Compound | Alkali Metal/Al Ratio | Si/Al Ratio | Degree of Crystallinity (%) | Hydroxyl Group Peak Position (cm$^{-1}$) | Reaction Result on 50 hours (*3) DME Conversion (%) | Propylene Yield (c-mol %) |
|---|---|---|---|---|---|---|---|---|---|
| Example 12 | LiCl | 20.0 | none | 0 | 2525 | 101 | 3728.7 | 100.0 | 38.6 |
| Example 13 | KNO$_3$ | 20.0 | none | 0 | 2525 | 95 | 3728.9 | 100.0 | 38.5 |
| Example 14 | NaOH | 20.0 | none | 0 | 2525 | 96 | 3729.1 | 100.0 | 39.0 |
| Example 15 | none | 0.0058 | Cs$_2$CO$_3$ | 20.0 | 2525 | 100 | 3729.5 | 100.0 | 38.8 |
| Example 16 | K in TPAOH | 21.4 | none | 0 | 2525 | 102 | 3729.2 | 100.0 | 39.0 |
| Example 17 | sodium aluminate | 1.5 | KCl | 20.0 | 2525 | 108 | 3728.4 | 100.0 | 38.9 |

(*1)Alkali metal compound used in the step of preparing the starting material shaped body, and alkali meta/aluminium atomic ratio.
(*2)Alkali metal compound added to binderless crystalline aluminosilicate shaped body, and alkali meta/aluminium atomic ratio.
(*3)Reaction temperature: 450° C., WHSV of DME: 1.0 hr$^{-1}$.

TABLE 3

| Example | Physical Data of Propylene Production Catalyst Alkali Metal/Al Ratio before Firing in Second Step | Si/Al Ratio | Crystal Structure | Degree of Crystallinity | Hydroxyl Group Peak Position (cm$^{-1}$) | Reaction Result on 50 hours (*1) DME Conversion (%) | Yield of Reaction Product (c-mol %) (*3) methane | ethylene |
|---|---|---|---|---|---|---|---|---|
| Comparative Example 1 | 10.0 | 250 | MFI type | 102 | 3729.0 | 100.0 | 0.47 | 9.85 |
| Example 21 | 4.2 | 500 | MFI type | 108 | 3728.7 | 100.0 | 0.20 | 7.71 |
| Example 22 | 8.5 | 1000 | MFI type | 105 | 3729.0 | 100.0 | 0.20 | 5.62 |
| Example 23 | 12.5 | 1500 | MFI type | 99 | 3728.8 | 100.0 | 0.18 | 4.03 |
| Example 16 | 21.4 | 2525 | MFI type | 102 | 3729.2 | 100.0 | 0.19 | 3.63 |
| Example 24 | 42.8 | 5000 | MFI type | 97 | 3729.5 | 100.0 | 0.14 | 2.95 |
| Comparative Example 2 (*2) | 128.4 | 15000 | MFI type | 96 | — | 84.8 | 0.35 | 0.49 |
| Example 25 | 20.0 | 2525 | MEL type | 96 | 3729.3 | 100.0 | 0.16 | 3.95 |
| Comparative Example 3 | — | 500 | MFI type | 111 | — | 100.0 | 2.54 | 9.11 |

TABLE 3-continued

| | | Reaction Result on 50 hours (*1) | | | | | |
|---|---|---|---|---|---|---|---|
| | | Yield of Reaction Product (c-mol %) (*3) | | | | | |
| | Example | ethane | propylene | propane | C4 component (1) | C4 component (2) | propylene/ ethylene ratio (c-mol ratio) | propylene/ propane ratio (c-mol ratio) |
| | Comparative Example 1 | 0.26 | 23.26 | 4.51 | 13.47 | 11.31 | 2.36 | 5.16 |
| | Example 21 | 0.08 | 31.47 | 1.87 | 19.35 | 9.62 | 4.08 | 16.80 |
| | Example 22 | 0.04 | 34.73 | 1.19 | 20.93 | 9.06 | 6.18 | 29.15 |
| | Example 23 | 0.03 | 38.04 | 0.76 | 21.69 | 8.75 | 9.43 | 49.90 |
| | Example 16 | 0.03 | 38.95 | 0.62 | 20.94 | 8.50 | 10.74 | 63.09 |
| | Example 24 | 0.02 | 38.71 | 0.51 | 18.79 | 7.55 | 13.11 | 76.04 |
| | Comparative Example 2 (*2) | 0.02 | 19.22 | 0.11 | 9.75 | 4.31 | 39.60 | 174.21 |
| | Example 25 | 0.03 | 38.20 | 0.63 | 22.25 | 9.11 | 9.66 | 60.81 |
| | Comparative Example 3 | 0.11 | 28.41 | 3.09 | 16.90 | 13.49 | 3.12 | 9.21 |

(*1) Reaction temperature: 450° C., WHSV of DME: 1.0 hr$^{-1}$.
(*2) Reaction result on 24 hours.
(*3) C4 component (1): 1-butene + isobutene + cis-2-butene. C4 component (2): normal-butane + isobutane + trans-2-butene.

TABLE 4

| | | | | Reaction Result | | | | | | |
|---|---|---|---|---|---|---|---|---|---|---|
| | | | | Yield (c-mol %) (*3) | | | | | | propylene/ ethylene | propylene/ propane |
| Example | Starting Material | Reaction Time (hr) | DME Conversion (%) | methane | ethylene | ethane | propylene | propane | C4 component (1) | C4 component (2) | ratio (c-mol ratio) | ratio (c-mol ratio) |
| Example 26 (*1) | dimethyl ether | 100 | 100.0 | 0.3 | 4.6 | 0.0 | 48.7 | 0.1 | 21.2 | 7.3 | 10.5 | 414.7 |
| | | 500 | 100.0 | 0.3 | 3.6 | 0.0 | 46.1 | 0.1 | 19.6 | 7.1 | 12.7 | 639.4 |
| | | 1000 | 99.8 | 0.4 | 2.9 | 0.0 | 42.1 | 0.1 | 18.3 | 6.9 | 14.4 | 735.4 |
| Example 27 (*2) | methanol | 500 | 100.0 | 0.4 | 3.5 | 0.0 | 46.8 | 0.1 | 18.7 | 7.0 | 13.4 | 706.8 |

(*1) Reaction temperature: 500° C., DME WHSV: 2.0 hr$^{-1}$, reaction gas composition: DME/N2 = 60%/40%.
(*2) Reaction temperature: 500° C., MeOH WHSV: 2.4 hr$^{-1}$, reaction gas composition: MeOH/N2 = 75%/25%.
(*3) C4 component (1): 1-butene + isobutene + cis-2-butene. C4 component (2): normal-butane + isobutane + trans-2-butene.

TABLE 5

| | | Reaction Tube Outlet Port Gas Composition (c-mol %) (*2) | | | | | | | |
|---|---|---|---|---|---|---|---|---|---|
| Example | Reaction Starting Material | methane | ethylene | ethane | propylene | propane | C4 component (1) | C4 component (2) | C5 or more components |
| Example 28 | 1-butene | 0.03 | 2.92 | 0.02 | 27.17 | 0.18 | 38.55 | 14.20 | 16.94 |
| Example 29 | 1-hexene | 0.03 | 2.95 | 0.02 | 27.10 | 0.17 | 18.50 | 6.92 | 44.31 |
| Example 30 | ethylene | 0.00 | 98.83 | 0.02 | 0.22 | 0.00 | 0.70 | 0.24 | 0.00 |

(*1) Reaction temperature: 500° C., WHSV: 1.0 hr$^{-1}$, reaction gas composition: olefin/N2 = 50%/50%.
(*2) C4 component (1): 1-butene + isobutene + cis-2-butene. C4 component (2): normal-butane + isobutane + trans-2-butene.

TABLE 6

| | DME Conversion | Yield (c-mol %) (*3) | | | | | | |
|---|---|---|---|---|---|---|---|---|
| | (%) | methane | ethylene | ethane | propylene | propane | C4 component (1) | C4 component (2) |
| Example 31 (*1) | 100.0 | 0.3 | 11.5 | 0.2 | 47.5 | 1.7 | 21.3 | 7.6 |
| Example 32 (*2) | 100.0 | 0.4 | 11.4 | 0.1 | 47.2 | 1.4 | 19.3 | 6.6 |

(*1) Reaction temperature: 550° C., DME WHSV: 1.0 hr$^{-1}$, reaction gas composition: DME/ethylene/isobutene/H2O = 46%/3%/6%/45%.
(*2) Reaction temperature: 550° C., MeOH WHSV: 2.0 hr$^{-1}$, reaction gas composition: MeOH/ethylene/1-butene = 91%/3%/6%.
(*3) C4 component (1): 1-butene + isobutene + cis-2-butene. C4 component (2): normal-butane + isobutane + trans-2-butene.

The invention claimed is:

1. A propylene production catalyst for producing propylene from one or more selected from a group consisting of methanol, dimethyl ether and olefins having from 4 to 8 carbon atoms, which comprises a binderless crystalline aluminosilicate shaped body having a silicon/aluminum atomic ratio of from 500 to 10000 and in which the crystalline aluminosilicate contains an MFI-type crystal structure and/or an MEL-type crystal structure;

wherein the peak position for the hydroxyl group in the binderless crystalline aluminosilicate shaped body to be detected within a range of from 3715 $cm^{-1}$ to 3735 $cm^{-1}$ in IR spectrometry falls within a range of from 3725 $cm^{-1}$ to 3735 $cm^{-1}$.

2. The propylene production catalyst according to claim 1, wherein the crystalline aluminosilicate is an MFI-type crystal structure and/or an MEL-type crystal structure.

3. The propylene production catalyst according to claim 1, wherein the cation type of the crystalline aluminosilicate is a proton type or an ammonium ion type.

* * * * *